United States Patent

Miura et al.

[11] Patent Number: 5,037,575
[45] Date of Patent: Aug. 6, 1991

[54] SQUARILIUM COMPOUND AND LIQUID CRYSTAL COMPOSITION CONTAINING THE SAME

[75] Inventors: Konoe Miura, Kanagawa; Tetsuo Ozawa, Tokyo; Junko Iwanami, Kanagawa, all of Japan

[73] Assignee: Mitsubishi Chemical Industries Ltd., Tokyo, Japan

[21] Appl. No.: 605,215

[22] Filed: Oct. 29, 1990

Related U.S. Application Data

[63] Continuation of Ser. No. 228,405, Aug. 5, 1988, abandoned, which is a continuation of Ser. No. 809,674, Dec. 16, 1985, abandoned.

[30] Foreign Application Priority Data

| Dec. 19, 1984 | [JP] | Japan | 59-267890 |
| Feb. 13, 1985 | [JP] | Japan | 60-25662 |
| Mar. 23, 1985 | [JP] | Japan | 60-57561 |
| Mar. 23, 1985 | [JP] | Japan | 60-57562 |
| Apr. 16, 1985 | [JP] | Japan | 60-81893 |
| Apr. 23, 1985 | [JP] | Japan | 60-87243 |
| May 15, 1985 | [JP] | Japan | 60-101580 |
| Jun. 27, 1985 | [JP] | Japan | 60-141096 |
| Jun. 27, 1985 | [JP] | Japan | 60-141097 |

[51] Int. Cl.$^5$ .......................... G03G 5/06; G02F 1/13
[52] U.S. Cl. .................... 252/299.1; 430/70; 430/57; 430/75; 430/78; 359/96
[58] Field of Search ............... 350/349; 430/70, 71, 430/72, 73, 74, 75, 20, 79; 548/427, 450; 568/381, 839; 546/93; 549/43, 44, 45, 458; 252/299.1, 299.01

[56] References Cited

U.S. PATENT DOCUMENTS

| 4,175,956 | 11/1979 | Haley et al. | 430/37 |
| 4,481,270 | 11/1984 | Kubota et al. | 430/72 |
| 4,548,886 | 10/1985 | Katagiri et al. | 430/70 |
| 4,565,761 | 1/1986 | Katagiri et al. | 430/75 |
| 4,579,799 | 4/1986 | Katagiri et al. | 430/72 |
| 4,606,613 | 8/1986 | Urabe | 350/349 |
| 4,629,670 | 12/1986 | Katagiri et al. | 430/70 |
| 4,738,908 | 4/1988 | Ogachi et al. | 430/20 |

FOREIGN PATENT DOCUMENTS

| 153729 | 9/1985 | European Pat. Off. | 430/71 |
| 196919 | 10/1986 | European Pat. Off. | 252/299.1 |
| 361299 | 9/1988 | European Pat. Off. | 252/299.01 |
| 59-191059 | 10/1984 | Japan | 430/71 |
| 59-197485 | 11/1984 | Japan | 430/71 |
| 60-262163 | 12/1985 | Japan | 430/71 |
| 60-263946 | 12/1985 | Japan | 430/71 |
| 61-185487 | 8/1986 | Japan | 252/299.1 |
| 62-124987 | 6/1987 | Japan | 252/299.1 |
| 62-130890 | 6/1987 | Japan | 252/299.1 |
| 1149890 | 12/1987 | Japan | 252/299.1 |
| 2140023 | 11/1984 | United Kingdom | |
| 2156089 | 10/1985 | United Kingdom | |

OTHER PUBLICATIONS

Loutfy et al., Photographic Science & Eng., 27(1), pp. 5–9 (1983).

*Primary Examiner*—Robert L. Stoll
*Assistant Examiner*—Greg M. Sweet
*Attorney, Agent, or Firm*—Sughrue, Mion, Zinn, Macpeak & Seas

[57] ABSTRACT

A squarilium compound represented by the following formula (I) and a liquid crystal composition containing the same are disclosed:

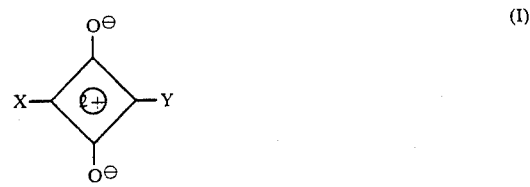

wherein X and Y each represents (Abstract continued on next page.)

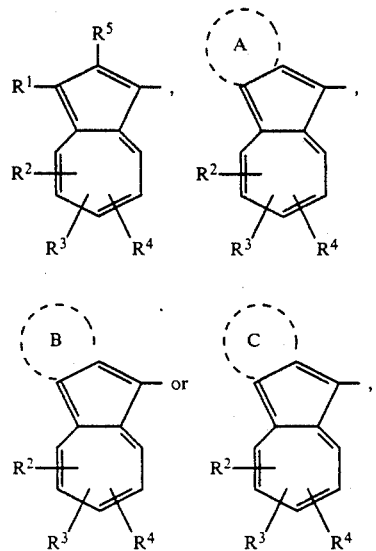

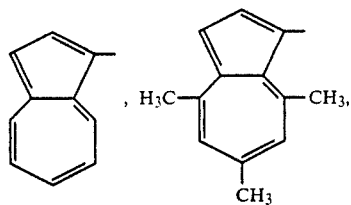

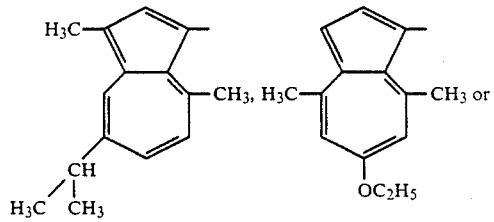

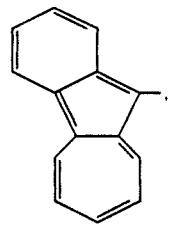

wherein $R^1$ represents a hydrogen atom, an alkyl group, a substituted or unsubstituted aryl group or a substituted or unsubstituted aralkyl group; $R^2$, $R^3$ and $R^4$ each represents a hydrogen atom, an alkyl group or a substituted or unsubstituted alkoxy group; $R^5$ represents a hydrogen atom, an alkyl group, an aralkyl group or an aryl group; ring A represents a cyclic alkylene; ring B represents a substituted or unsubstituted aromatic ring; and ring C represents a heterocyclic ring containing one or two of a nitrogen atom, an oxygen atom and a sulfur atom; with proviso that X and Y are not the same when either one of them represents and a liquid crystal composition containing the squarilium compound of the formula (I). The squarilium compound (I) are soluble in a wide variety of solvents and resistant to light, and their maximum absorption wavelengths in these solvents are in the ranges of from 700 to 900 nm.

13 Claims, 1 Drawing Sheet

SQUARILIUM COMPOUND AND LIQUID CRYSTAL COMPOSITION CONTAINING THE SAME

This is a continuation of application Ser. No. 228,405 filed Aug. 5, 1988, now abandoned, which is a continuation of Ser. No. 809,674 filed Dec. 16, 1985, now abandoned.

FIELD OF THE INVENTION

This invention relates to a squarilium compound and a liquid crystal composition containing the same.

BACKGROUND OF THE INVENTION

An information recording system using laser beams has recently been studied, wherein a liquid crystal having dissolved therein a compound which absorbs a laser beam of specific wavelengths is heated by irradiation of such a laser beam, whereupon the state of the irradiated portion is changed, for example, from an isotropically aligned state to a scattered state, as described, e.g., in *IBM Tech. Discl. Bull.*, 21, 2007 (1978).

On the other hand, it is known that a squarilium compound has photoconductivity and can be used, e.g., as an electric charge generator for electrophotographic light-sensitive materials (Japanese Patent Application (OPI) No. 105536/74, the term "OPI" as herein used referring to "published unexamined application"), a laser beam-absorbing material for laser recording liquid crystal display devices (Japanese Patent Application (OPI) No. 197485/84) and as a recording material for photodiscs (Japanese Patent Application (OPI) Nos. 46221/81, 217758/83 and 129954/84).

However, conventionally known squarilium compounds involve problems of solubility such that they are soluble only in limited solvents, such as aprotic polar solvents, e.g., N,N-dimethylformamide, N-methylpyrrolidone, N,N-dimethylacetamide, formamide, dimethyl sulfoxide, etc., and also some of them have very poor solubility as in the case of Compound No. 6 disclosed in Japanese Patent Application (OPI) No. 129954/84. Further, many of these known compounds not only have the maximum absorption wavelengths in their solutions far aside from the oscillation wavelengths of semiconductor lasers, i.e., 780 nm, 830 nm or 850 nm but also lack in stability due to their insufficient light-resistance.

The conventional squarilium compounds can, therefore, find only limited applications and are not satisfactorily applicable to various information recording materials, particularly those using a laser beam as a light source.

SUMMARY OF THE INVENTION

Accordingly, an object of this invention is to provide a novel squarilium compound which can eliminate the above-described problems associated with the known squarilium compounds, as well as a liquid crystal composition containing such a novel squarilium compound.

That is, the present invention relates to a squarilium compound represented by the formula (I):

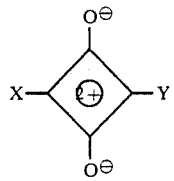

wherein X and Y each represents

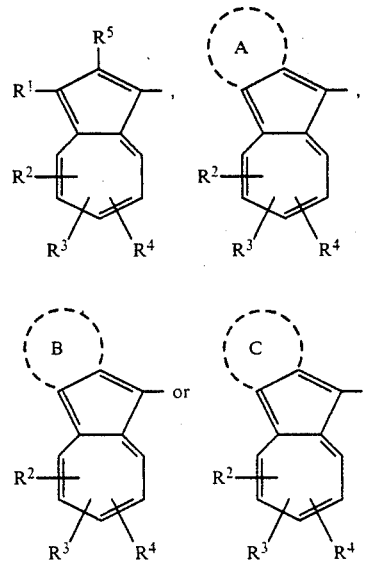

wherein $R^1$ represents a hydrogen atom, an alkyl group, a substituted or unsubstituted aryl group or a substituted or unsubstituted aralkyl group; $R^2$, $R^3$ and $R^4$ each represents a hydrogen atom, an alkyl group or a substituted or unsubstituted alkoxy group; $R^5$ represents a hydrogen atom, an alkyl group, an aralkyl group or an aryl group; ring A represents a cyclic alkylene; ring B represents a substituted or unsubstituted aromatic ring; and ring C represents a heterocyclic ring containing one or two of a nitrogen atom, an oxygen atom and a sulfur atom; with proviso that X and Y are not the same when either one of them represents

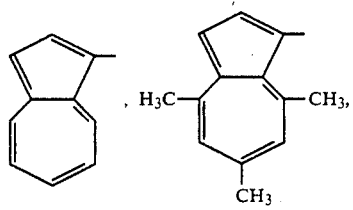

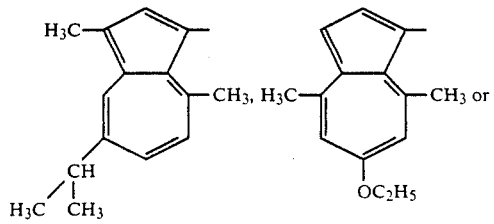

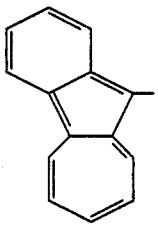

and a liquid crystal composition containing the squarilium compound of the formula (I).

DETAILED DESCRIPTION OF THE INVENTION

Figure 1:
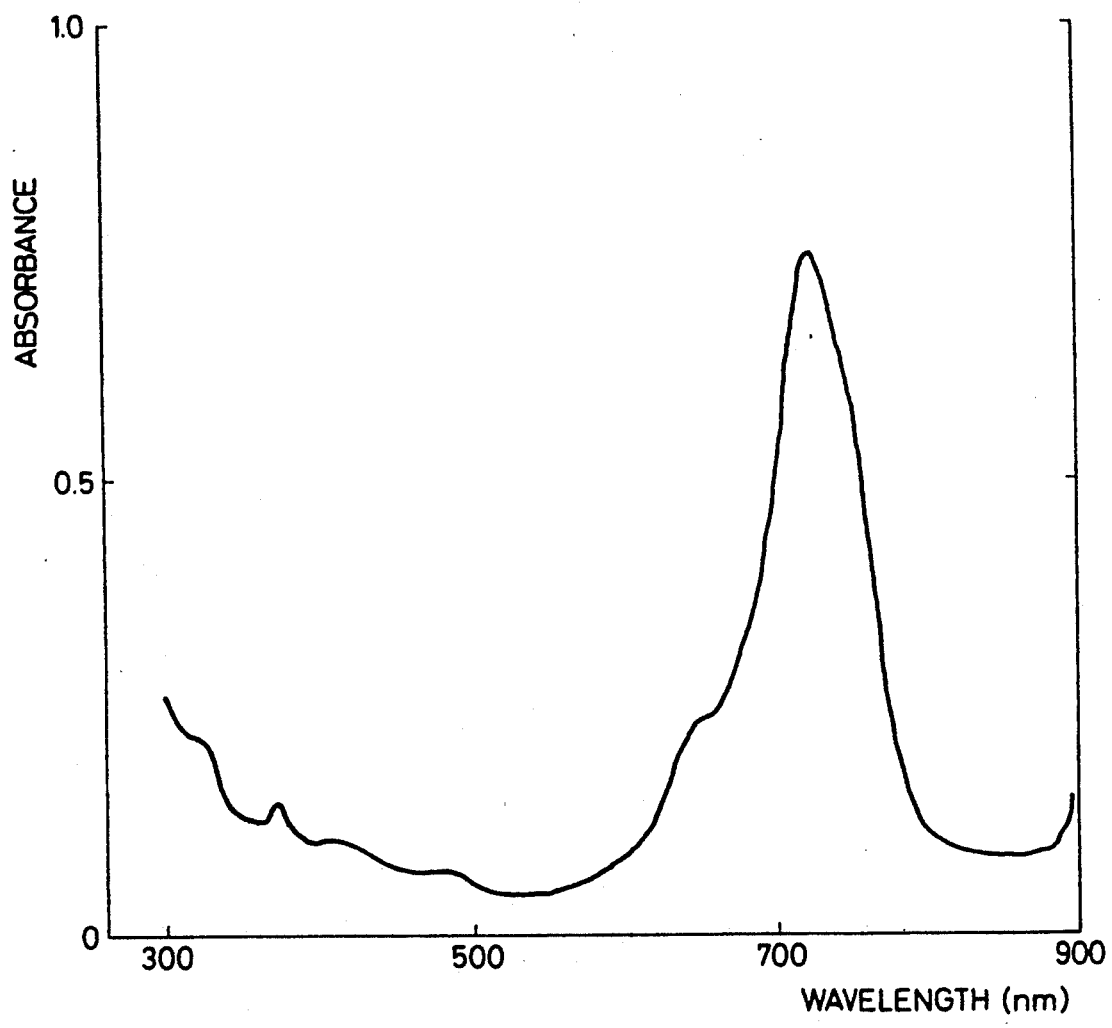
FIG. 1 shows a visible to infrared absorption spectrum of the squarilium compound according to Example 264 of this invention in a chloroform solution.

The compound represented by the formula (I) according to the present invention can easily be prepared by, for example, reacting an azulene derivative represented by the formula (II) or (III):

$$X-H \quad (II)$$

$$Y-H \quad (III)$$

wherein X and Y are as defined above, with 3,4-dihydroxy-3-cyclobutene-1,2-dione, i.e., squaric acid, represented by the formula:

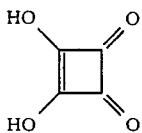

in a solvent.

The solvent which can be used in the above reaction includes alcohols, e.g., methanol, ethanol, 1-propanol, isopropyl alcohol, 1-butanol, 2-butanol, amyl alcohol, 1-hexanol, cyclohexanol, 1-heptanol, 1-nonanol, etc.; and mixed solvents of these alcohols and aromatic hydrocarbons, e.g., benzene, toluene, xylene, chlorobenzene, etc.

The reaction temperature is selected from to 150° C., and preferably from 90° to 120° C.

The starting compound represented by the formula (II) or (III) includes the azulene derivatives as follows:

(a) The position numbering system of the azulene derivatives shown below is

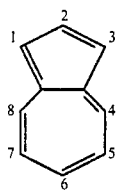

Azulene
1,5,8-Trimethylazulene
1,6,8-Trimethylazulene
4,6,8-Trimethylazulene
6-Isopropyl-4,8-dimethylazulene
6-t-Butyl-4,8-dimethylazulene
1-Methyl-2-ethyl-5-isopropylazulene
1-Methyl-2-ethyl-6-methylazulene
1-Ethyl-2-n-propyl-5-isopropylazulene
1-Ethyl-2-n-propyl-6-isopropylazulene
1-n-Propyl-2-n-butyl-5-isopropylazulene
1-Isopropyl-2-isopropyl-5-isopropylazulene
1-n-Butyl-2-n-pentyl-5-isopropylazulene
1-n-Pentyl-2-n-hexyl-6-isopropylazulene
1-n-Hexyl-2-n-octyl-6-isopropylazulene
1-n-Octyl-2-n-hexyl-6-isopropylazulene
1-n-Decyl-2-n-undecyl-5-isopropylazulene
1,4-Dimethyl-7-isopropylazulene
1-n-Dodecyl-2-n-tridecyl-5-isopropylazulene
1-Methyl-8-methoxyazulene
1-Ethyl-8-methoxyazulene
1-Methyl-5-isopropylazulene
1-Ethyl-5-isopropylazulene
1-n-Propyl-5-isopropylazulene
1-Isopropyl-5-isopropylazulene
1-Butyl-5-isopropylazulene
1-Methyl-6-isopropylazulene
1-Propyl-6-isopropylazulene
1-n-Octyl-5-isopropylazulene
1-n-Decyl-5-isopropylazulene
1-n-Octadecyl-5-isopropylazulene
1-Methyl-5-methyl-8-methylazulene
1-Methyl-6-methyl-8-methylazulene
1-n-Butyl-5-isopropyl-8-methoxyazulene
1-n-Propyl-5-isopropyl-8-n-hexyloxyazulene
1-Ethyl-5-isopropyl-8-n-octadecyloxyazulene
1-n-Pentyl-5-isopropyl-8-ethoxyethoxyazulene
1-n-Tetradecylazulene
1-n-Pentadecylazulene
1-n-Hexadecylazulene
1-n-Heptadecylazulene
1-n-Octadecylazulene
1-n-Nonadecylazulene
1-n-Eicosylazulene
1-n-Heneicosylazulene
1-n-Docosylazulene
1-n-Tricosylazulene
1-n-Tetracosylazulene
1-n-Pentacosylazulene
1-n-Tetradecyl-5-isopropylazulene
1-n-Hexadecyl-5-isopropylazulene
1-n-Heptadecyl-5-isopropylazulene
1-n-octadecyl-5-isopropylazulene
1-n-Eicosyl-5-methylazulene
1-n-Docosyl-5-methylazulene
1-n-Tetracosyl-5-methylazulene
1-n-Pentadecyl-6-isopropylazulene
1-n-Heptadecyl-6-isopropylazulene
1-n-Octadecyl-6-methylazulene
1-n-Heneicosyl-6-methylazulene
1-n-Pentadecyl-8-methoxyazulene
1-n-Heptadecyl-8-methoxyazulene
1-n-Octadecyl-8-methoxyazulene
1-n-Heptadecyl-8-methoxyethoxyazulene
1-n-Heptadecyl-8-heptadecyloxyazulene
1-n-Hexadecyl-5-isopropyl-8-methoxyazulene
1-n-Heptadecyl-5-isopropyl-8-methoxyazulene
1-n-Octadecyl-5-isopropyl-8-methoxyazulene
1-n-Pentadecyl-5-methyl-8-methoxyazulene
1-n-Nonadecyl-5-methyl-8-methoxyethoxyethoxyazulene
1-n-Tetradecyl-6-isopropyl-8-methoxyazulene 1-n-Heptadecyl-6-isopropyl-8-methoxyazulene
1-n-Heptadecyl-6-isopropyl-8-ethoxyazulene
1-n-Octadecyl-6-isopropyl-8-methoxyazulene
1-n-Tetradecyl-5-isopropyl-8-octadecyloxyazulene
1-n-Pentadecyl-2-n-tetradecylazulene
1-n-Tetradecyl-2-n-pentadecylazulene
1-n-Tetradecyl-2-n-pentadecyl-5-isopropylazulene
1-n-Hexadecyl-2-n-heptadecyl-5-isopropylazulene
1-Phenylazulene
1-Phenyl-5-methylazulene
1-Phenyl-6-methylazulene
1-Phenyl-5-isopropylazulene
1-Phenyl-6-isopropylazulene
1-(p-Methylphenyl)-6-isopropylazulene
1-(m-Methylphenyl)-5-isopropylazulene
1-(p-Ethylphenyl)-5-methylazulene
1-(p-Ethylphenyl)-6-isopropylazulene
1-(p-n-Propoxyphenyl)-5-isopropylazulene
1-(p-n-Butylphenyl)-5-isopropylazulene
1-(p-n-Butoxyphenyl)-5-isopropylazulene
1-(p-n-Pentylphenyl)-5-isopropylazulene
1-(p-n-Hexylphenyl)-6-isopropylazulene
1-(p-n-Heptylphenyl)-5-isopropylazulene
1-(p-n-Heptylphenyl)-6-methylazulene
1-(p-n-Octylphenyl)-5-isopropylazulene
1-(p-t-Butylphenyl)-5-isopropylazulene
1-(p-t-Butylphenyl)-6-isopropylazulene
1-(p-Fluorophenyl)-5-isopropylazulene
1-(p-Chlorophenyl)-6-isopropylazulene
1-(m-Bromophenyl)-5-isopropylazulene
1-Benzyl-5-isopropylazulene
1-Benzyl-6-isopropylazulene
1-Benzyl-5-methylazulene
1-(m-Bromobenzyl)-6-methylazulene
1-(p-Methylbenzyl)-5-isopropylazulene
1-(p-n-Butylbenzyl)-5-isopropylazulene
1-(p-n-Hexyloxybenzyl)-6-isopropylazulene
1-(p-n-Octylbenzyl)-6-isopropylazulene
1-Phenethyl-5-isopropylazulene
1-(p-Methylphenethyl)-6-isopropylazulene
1,2-Trimethylene-5-isopropylazulene
1,2-Trimethylene-6-isopropylazulene
1,2-Trimethylene-5-methylazulene
1,2-Trimethylene-6-methylazulene
1,2-Trimethyleneazulene
1,2-Tetramethyleneazulene
1,2-Tetramethylene-5-methylazulene
1,2-Tetramethylene-6-methylazulene
1,2-Tetramethylene-5-isopropylazulene
1,2-Tetramethylene-6-isopropylazulene
1,2-pentamethylene-5-methylazulene
1,2-Pentamethylene-6-methylazulene
1,2-Pentamethylene-5-isopropylazulene
1,2-Pentamethylene-6-isopropylazulene
1,2-Hexamethylene-5-isopropylazulene
1,2-Hexamethylene-6-isopropylazulene
1,2-Decamethylene-5-isopropylazulene
1,2-Decamethylene-6-isopropylazulene (b) The position numbering system of the following benz[a]azulene derivatives is

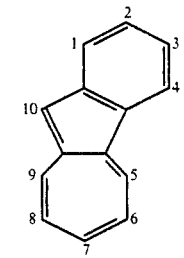

Benz[a]azulene
1,2,3,4-Tetrahydro-3-methyl-benz[a]azulene
1,2,3,4-Tetrahydro-3-t-butyl-benz[a]azulene
7-Isopropyl-benz[a]azulene
8-Isopropyl-benz[a]azulene
3-Ethyl-8-isopropyl-benz[a]azulene
3-t-Butyl-benz[a]azulene
3-t-Butyl-8-isopropyl-benz[a]azulene
3-n-Pentyl-8-isopropyl-benz[a]azulene
3-n-Heptyl-7-methyl-benz[a]azulene
3-n-Heptyl-8-isopropyl-benz[a]azulene
3-n-Octyl-8-isopropyl-benz[a]azulene
2-Methoxy-8-isopropyl-benz[a]azulene
2-n-Butoxy-8-methyl-benz[a]azulene
3-Methoxy-7-isopropyl-benz[a]azulene
3-Methoxy-8-isopropyl-benz[a]azulene
3-Bromo-8-isopropyl-benz[a]azulene
3-Ethyl-5-methoxy-8-isopropyl-benz[a]azulene
3-n-Butyl-5-methoxy-8-isopropyl-benz[a]azulene
3-n-Propyl-5-butoxy-7-isopropyl-benz[a]azulene
5-Ethoxyethoxy-8-isopropyl-benz[a]azulene
3-Ethyl-7-isopropyl-benz[a]azulene
3-n-Propyl-7-isopropyl-benz[a]azulene
3-n-Propyl-8-isopropyl-benz[a]azulene
3-n-Butyl-8-isopropyl-benz[a]azulene
3-n-Hexyl-7-isopropyl-benz[a]azulene
3-n-Heptyl-8-methyl-benz[a]azulene
3-n-Octyl-8-methyl-benz[a]azulene
3-n-Tridecyl-8-methyl-benz[a]azulene
2-n-Butoxy-8-isopropyl-benz,:a]azulene
2-n-Heptyloxy-8-isopropyl-benz[a]azulene
3-Methoxy-8-isopropyl-benz[a]azulene
3-t-Butyl-5-methoxy-8-isopropyl-benz[a]azulene
3-Ethyl-5-n-butoxy-8-isopropyl-benz[a]azulene
3-n-Propyl-5-n-octyloxy-7-isopropyl-benz[a]azulene
5-n-Tridecyloxy-8-isopropyl-benz[a]azulene
2-Methoxyethoxy-8-isopropyl-benz[a]azulene
2-Ethoxyethoxyethoxy-8-isopropyl-benz[a]azulene
5-Methoxyethoxyethoxy-8-isopropyl-benz[a]azulene
3-n-Pentyl-benz[a]azulene
3-n-Heptyl-benz[a]azulene
3-n-Propyl-benz[a]azulene
3-t-Butyl-8-isopropyl-benz[a]azulene
7-Isopropyl-benz[a]azulene
3-n-Hexyl-benz[a]azulene
3-n-Octyl-8-isopropyl-benz[a]azulene
3-n-Pentyl-7-isopropyl-benz[a]azulene
3-n-Butyl-7-isopropyl-benz[a]azulene (c) The position numbering system of the following azuleno[1,2-b]thiophene derivatives is

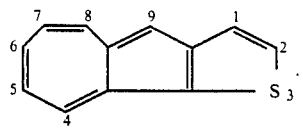

Azuleno[1,2-b]thiohene
7-Methylazuleno[1,2-b]thiophene
7-Isopropylazuleno[1,2-b]thiophene
6-Methylazuleno[1,2-b]thiophene
6-Isopropylazuleno[1,2-b]thiophene
4-Methoxy-7-isopropylazuleno[1,2-b]thiophene
4-Butoxy-7-isopropylazuleno[1,2-b]thiophene
4-Octyloxy-6-isopropylazuleno[1,2-b]thiophene
4-Ethoxyethoxy-7-isopropylazuleno[1,2-b]thiophene
4-Methoxyethoxyethoxy-7-isopropylazuleno[1,2-b]-thiophene
1,4,8-Trimethylazuleno[1,2-b]thiophene
4-Tridecyloxy-7-isopropylazuleno[1,2-b]thiophene
4-Octadecyloxy-7-isopropylazuleno[1,2-b]thiophene
Azuleno[1,2-b]1,2-dihydroxythiophene
7-Isopropylazuleno[1,2-b]1,2-dihydrothiophene
6-Isopropylazuleno[1,2-b]1,2-dihydrothiophene
7-Methylazuleno[1,2-b]1,2-dihydrothiophene
4-Methoxy-7-isopropylazuleno[1,2-b]1,2-dihydrothiophene
4-Hepthyloxy-7-isopropylazuleno[1,2-b]1,2-dihydrothiophene
4-Octadecyloxy-7-isopropylazuleno[1,2-b]1,2-dihydrothiophene
4-Methoxy-6-isopropylazuleno[1,2-b]1,2-dihydrothiophene
4-Methoxyazuleno[1,2-b]1,2-dihydrothiophene
2-Methyl-7-isopropylazuleno[1,2-b]thiophene
4-Methoxyethoxy-7-isopropylazuleno[1,2-b]1,2-dihydrothiophene
2-Methylazuleno[1,2-b]thiophene
4-Methoxyazuleno[1,2-b]thiophene
1,2-Diphenylazuleno[1,2-b]thiophene
4,6,8-Trimethyl-2-phenylazuleno[1,2-b]thiophene (d) The position numbering system of the following azuleno[2,1-b]thiophene derivatives is

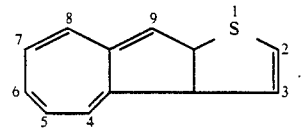

Azuleno[2,1-b]thiophene
7-Methylazuleno[2,1-b]thiophene
7-Isopropylazuleno[2,1-b]thiophene
6-Methylazuleno[2,1-b]thiophene
6-Isopropylazuleno[2,1-b]thiophene
4-Methoxy-7-isopropylazuleno[2,1-b]thiophene
4-Butoxy-7-isopropylazuleno[2,1-b]thiophene
4-Octyloxy-6-isopropylazuleno[2,1-b]thiophene
4-Ethoxyethoxy-7-isopropylazuleno[2,1-b]thiophene
4-Methoxyethoxyethoxy-7-isopropylazuleno[2,1-b]-thiophene
4-Dodecyloxy-7-isopropylazuleno[2,1-b]thiophene
4-Octadecyloxy-7-isopropylazuleno[2,1-b]thiophene
Azuleno[2,1-b]2,3-dihydrothiophene
7-Isopropylazuleno[2,1-b]2,3-dihydrothiophene
6-Isopropylazuleno[2,1-b]2,3-dihydrothiophene
7-Methylazuleno[2,1-b]2,3-dihydrothiophene
4-Methoxy-7-isopropylazuleno[2,1-b]2,3-dihydrothiophene
4-Heptyloxy-7-isopropylazuleno[2,1-b]2,3-dihydrothiophene 4-Octadecyloxy-7-isopropylazuleno[2,1-b]2,3-dihydrothiophene
4-Methoxy-6-isopropylazuleno[2,1-b]2,3-dihydrothiophene
4-Methoxyazuleno[2,1-b]2,3-dihydrothiophene
2-Ethoxycarbonylazuleno[2,1-b]thiophene
3-Methylazuleno[2,1-b]thiophene
3-Methoxyazuleno[2,1-b]thiophene
4-Methoxyethoxy-7-isopropylazuleno[2,1-b]2,3-dihydrothiophene
4-Methoxyazuleno[2,1-b]thiophene (e) The position numbering system of the following azuleno[1,2-c]thiophene derivatives is

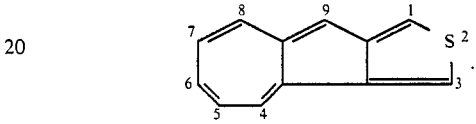

Azuleno[1,2-c]thiophene
7-Methylazuleno[1,2-c]thiophene
7-Isopropylazuleno[1,2-c]thiophene
6-Methylazuleno[1,2-c]thiophene
6-Isopropylazuleno[1,2-c]thiophene
4-Methoxy-7-isopropylazuleno[1,2-c]thiophene
4-Butoxy-7-isopropylazuleno[1,2-c]thiophene
4-Octyloxy-6-isopropylazuleno[1,2-c]thiophene
4-Ethoxyethoxy-7-isopropylazuleno[1,2-c]thiophene
4-Methoxyethoxyethoxy-7-isopropylazuleno[1,2-c]thiophene
4-Octadecyloxy-7-isopropylazuleno[1,2-c]thiophene
Azuleno[1,2-c]1,3-dihydrothiophene
7-Isopropylazuleno[1,2-c]1,3-dihydrothiophene
6-Isopropylazuleno[1,2-c]1,3-dihydrothiophene
7-Methylazuleno[1,2-c]1,3-dihydrothiophene
4-Methoxy-7-isopropylazuleno[1,2-c]1,3-dihydrothiophene
4-Heptyloxy-7-isopropylazuleno[1,2-c]1,3-dihydrothiophene
4-Octadecyloxy-7-isopropylazuleno[1,2-c]1,3-dihydrothiophene
4-Methoxy-6-isopropylazuleno[1,2-c]1,3-dihydrothiophene
4-Methoxyazuleno[1,2-c,1,3-dihydrothiophene
4-Methoxyethoxy-7-isopropylazuleno[1,2-c]1,3-dihydrothiophene
4-Methoxyazuleno[1,2-c]thiophene (f) The position numbering system of the following azuleno[1,2-b]furan derivatives is

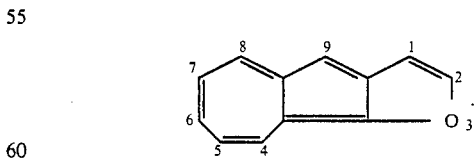

Azuleno[1,2-b]furan
7-Methylazuleno[1,2-b]furan
7-Isopropylazuleno[1,2-b]furan
6-Methylazuleno[1,2-b]furan
6-Isopropylazuleno[1,2-b]furan
4-Methoxy-7-isopropylazuleno[1,2-b]furan
4-Butoxy-7-isopropylazuleno[1,2-b]furan 4-Octyloxy-6-isopropylazuleno[1,2-b]furan
4-Ethoxyethoxy-7-isopropylazuleno[1,2-b]furan
4-Methoxyethoxyethoxy-7-isopropylazuleno[1,2-b]furan
4-Octadecyloxy-7-isopropylazuleno[1,2-b]furan
4-Methoxyazuleno[1,2-b]furan (g) The position numbering system of the following azuleno[1,2-b]pyrrole derivatives is

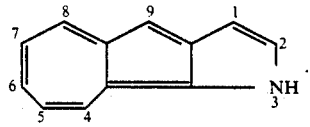

Azuleno[1,2-b]pyrrole
7-Methylazuleno[1,2-b]pyrrole
7-Isopropyl1,2-b]pyrrole
6-Isopropyl[1,2-b]pyrrole
3-Ethoxycarbonylazuleno[1,2-b]pyrrole
3-Ethoxycarbonyl-7-isopropylazuleno[1,2-b]pyrrole
3-Ethoxycarbonyl-6-isopropylazuleno[1,2-b]pyrrole (h) The position numbering system of the following azuleno[1,2-c]pyridine derivatives is

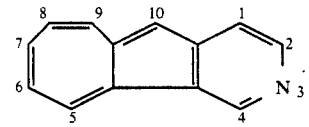

Azuleno[1,2-c]pyridine
8-Methylazuleno[1,2-c]pyridine
8-Isopropylazuleno[1,2-c]pyridine
7-Isopropylazuleno[1,2-c]pyridine
3-Ethoxycarbonylazuleno[1,2-c]1,2,3,4-tetrahydropyridine
3-Ethoxycarbonyl-8-isopropylazuleno[1,2-c]1,2,3,4-tetrahydropyridine
3-Ethoxycarbonyl-7-isopropylazuleno[1,2-c]1,2,3,4-tetrahydropyridine (i) The position numbering system of the following azuleno[2,1-c]pyridine derivatives is

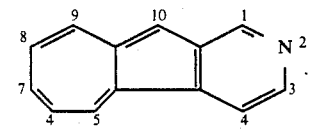

Azuleno[2,1-c]pyridine
Methylazuleno[2,1-c]pyridine
8-Isopropylazuleno[2,1-c]pyridine
7-Isopropylazuleno[2,1-c]pyridine
Azuleno[2,1-c]1,2,3,4-tetrahydropyridine
Azuleno[2,1-c]3,4-dihydropyridine
2-Ethoxycarbonylazuleno[2,1-c]1,2,3,4-tetrahydropyridine
2-Ethoxycarbonyl-8-isopropylazuleno[2,1-c]1,2,3,4-tetrahydropyridine
2-Ethoxycarbonyl-7-isopropylazuleno[2,1-c]1,2,3,4-tetrahydropyridine (g) The position numbering system of the following azuleno[1,2-b]pyridine derivatives is

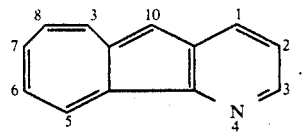

Azuleno[1,2-b]pyridine
4-Ethoxycarbonylazuleno[1,2-b]1,2,3,4-tetrahydropyridine
4-Ethoxycarbonyl-8-isopropylazuleno[1,2-b]1,2,3,4-tetrahydropyridine
4-Ethoxycarbonyl-7-isopropylazuleno[1,2-b]1,2,3,4-tetrahydropyridine (k) The position numbering system of the following azuleno[2,1-b]pyridine derivatives is

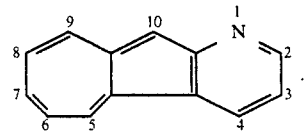

Azuleno[2,1-b]pyridine
2,3-Dichloroazuleno[2,1-b]pyridine
2-Methoxy-3-ethoxycarbonylazuleno[2,1-b]pyridine
2-Methylamino-3-ethoxycarbonylazuleno[2,1-b]pyridine
2-Methoxy-3-cyanoazuleno[2,1-b]pyridine Among the squarilium compounds represented by the formula (I), the squarilium compounds represented by the following formulae (IV) to (XXIII) are preferred.

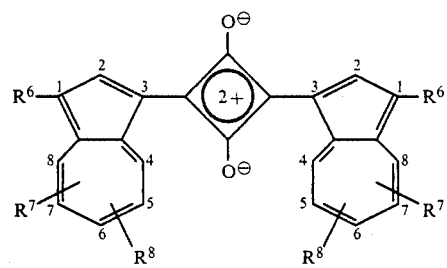

wherein $R^6$ represents a hydrogen atom or an alkyl group having from 1 to 13 carbon atoms; and $R^7$ and $R^8$ each represents a hydrogen atom, an alkyl group having from to 13 carbon atoms or an alkoxy group having from 1 to 13 carbon atoms, with proviso that $R^7$ and $R^8$ are positioned at the 5-, 6- or 8-position.

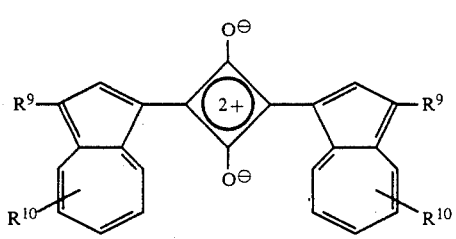

wherein $R^9$ represents a substituted or unsubstituted aryl group or a substituted or unsubstituted aralkyl group; and $R^{10}$ represents a hydrogen atom or an alkyl group having from 1 to 13 carbon atoms.

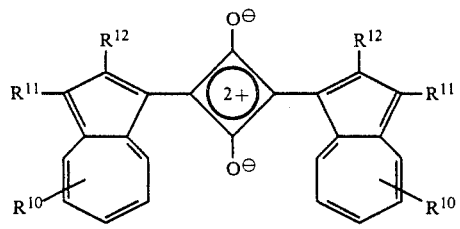

(VI)

wherein $R^{10}$ is as defined above; and $R^{11}$ and $R^{12}$ each represents an alkyl group having from 1 to 13 carbon atoms.

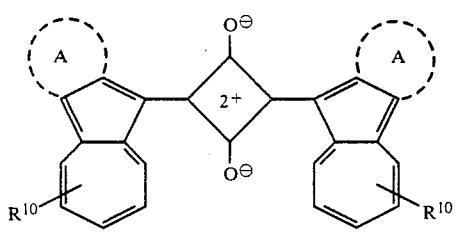

(VII)

wherein $R^{10}$ and ring A are as defined above.

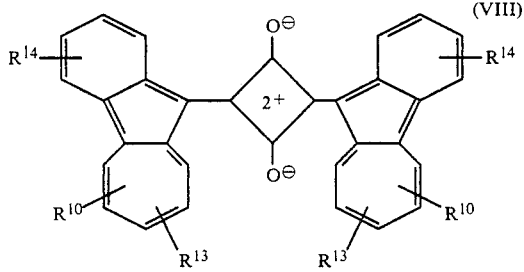

(VIII)

wherein $R^{10}$ is as defined above; $R^{13}$ represents a hydrogen atom or a substituted or unsubstituted alkoxy group having from 1 to 13 carbon atoms; and $R^{14}$ represents a hydrogen atom, a halogen atom, an alkyl group having from 1 to 13 carbon atoms or a substituted or unsubstituted alkoxy group having from 1 to 13 carbon atoms; with proviso that at least one of $R^{10}$, $R^{13}$ and $R^{14}$ represents an alkyl group having from 1 to 13 carbon atoms or a substituted or unsubstituted alkoxy group having from 1 to 13 carbon atoms.

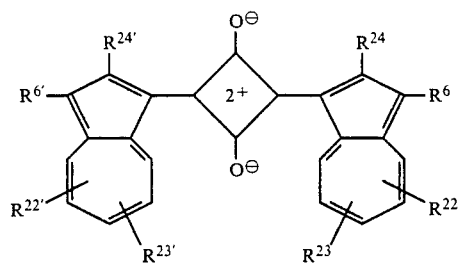

(IX)

wherein $R^6$ is as defined above; $R^{6'}$ has the same meanings as defined for $R^6$; $R^{22}$, $R^{22'}$, $R^{23}$ and $R^{23'}$ each represents a hydrogen atom, an alkyl group having from 1 to 13 carbon atoms or a substituted or unsubstituted alkoxy group having from 1 to 13 carbon atoms; $R^{24}$ and $R^{24'}$ each represents a hydrogen atom or alkyl group having from 1 to 13 carbon atoms; with proviso that at least one of the symmetrical pairs of $R^6$ and $R^{6'}$; $R^{22}$ and $R^{22'}$; $R^{23}$ and $R^{23'}$; and $R^{24}$ and $R^{24'}$ comprises different groups.

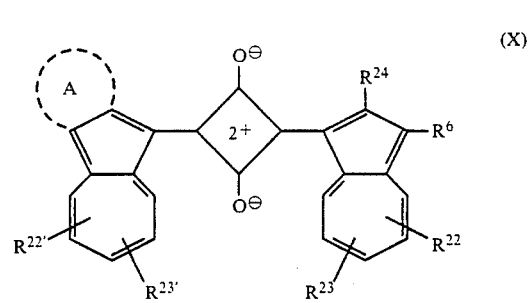

(X)

wherein $R^6$, $R^{22}$, $R^{22'}$, $R^{23}$, $R^{23'}$, $R^{24}$ and ring A are as defined above.

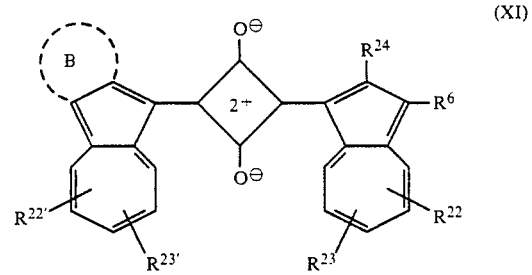

(XI)

wherein $R^6$, $1R^{22}$, $1R^{22'}$, $R^{23}$, $R^{23'}$, $R^{24}$ and ring B are as defined above.

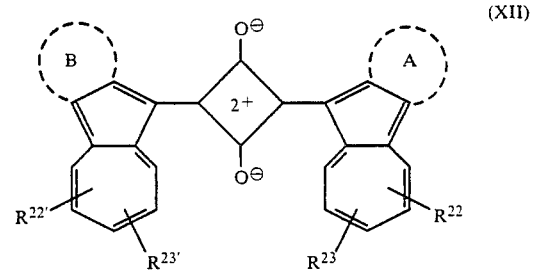

(XII)

wherein $R^{22}$, $R^{22'}$, $R^{23}$, $R^{23'}$, ring A and ring B are as defined above.

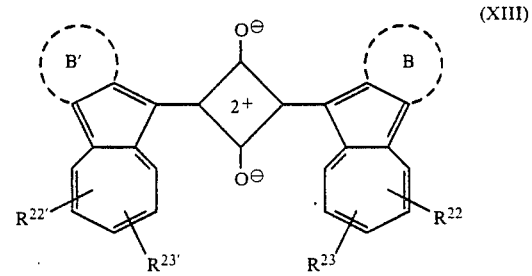

(XIII)

wherein $R^{22}$, $R^{22'}$, $R^{23}$, $R^{23'}$ and ring B are as defined above; and ring B' has the same meanings as ring B.

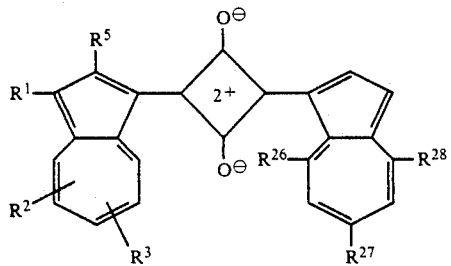

(XIV)

wherein $R^1$, $r^2$, $R^3$ and $R^5$ are as defined above; and $R^{26}$, $R^{27}$ and $lR^{28}$ each represents an alkyl group.

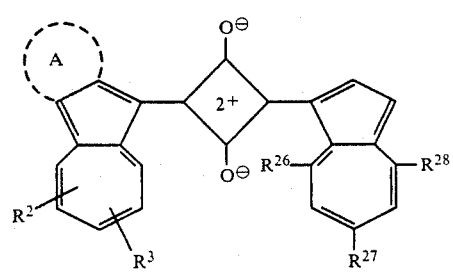

(XV)

wherein $R^2$, $r^3$, ring A, $R^{26}$, $lR^{27}$ and $R^{28}$ are as defined above.

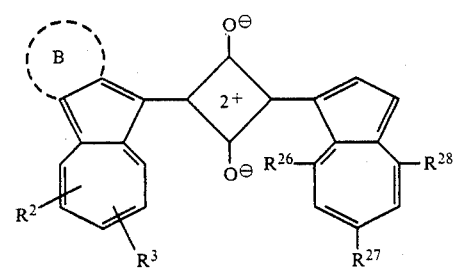

(XVI)

wherein $R^2$, $R^3$, $r^{26}$, $R^{27}$, $R^{28}$ and ring B are as defined above.

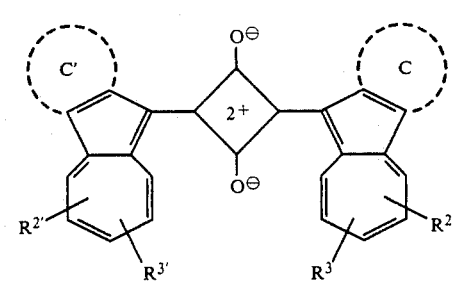

(XVII)

wherein $R^2$, $R^3$ and ring C are as defined above; $R^{2'}$ has the same meanings as $R^2$; $R^{3'}$ has the same meanings as $R^3$; and ring C' has the same meanings as ring C.

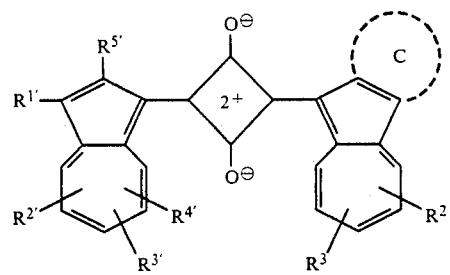

(XVIII)

wherein $R^2$, $R^3$, $lR^{2'}$, $R^{3'}$ and ring C are as defined above; $R^{1'}$ has the same meaning as $R^1$; $R^{4'}$ has the same meaning as $R^4$; and $R^{5'}$ has the same meaning as $R^5$.

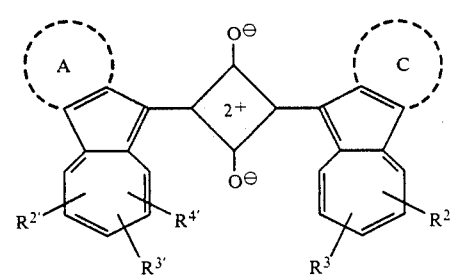

(XIX)

wherein $R^2$, $r^3$, $R^{2'}$, $R^{3'}$, $lR^{4'}$, ring A and ring C are as defined above.

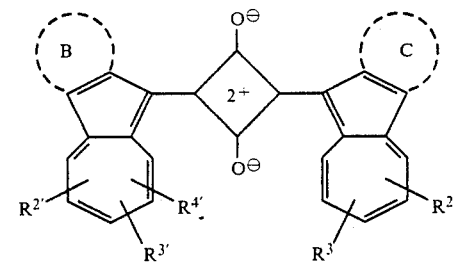

(XX)

wherein $R^2$, $R^3$, $R^{2'}$, $lR^{3'}$, $R^{4'}$, ring B and ring C are as defined above.

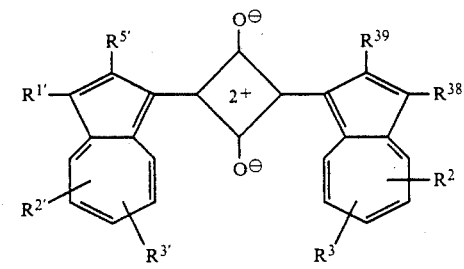

(XXI)

wherein $R^2$, $lR^3$, $R^{1'}$, $lR^{2'}$, $lR^{3'}$ and $R^{5'}$ are as defined above; and $R^{38}$ and $R^{39}$ represent a hydrogen atom or an alkyl group having from 14 to 25 carbon atoms; with proviso that at least one of $R^{38}$ and $R^{39}$ represents an alkyl group having from 14 to 25 carbon atoms.

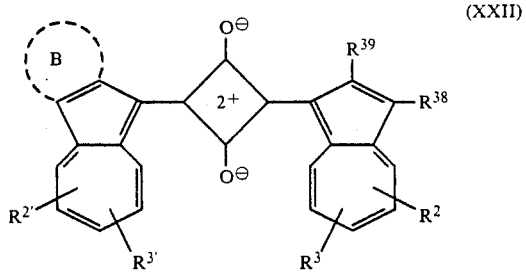

(XXII)

wherein $R^2$, $R^3$, $R^{2'}$, $R^{3'}$, $R^{38}$, $R^{39}$ and ring B are as defined above; with proviso that at least one of $R^{38}$ and $R^{39}$ represents an alkyl group having from 14 to 25 carbon atoms.

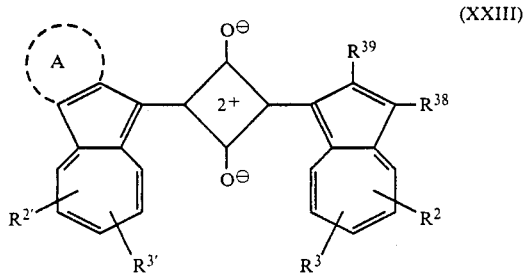

(XXIII)

wherein $R^2$, $R^3$, $R^{2'}$, $R^{3'}$, $R^{38}$, $R^{39}$ and ring A are as defined above; with proviso that at least one of $R^{38}$ and $R^{39}$ represents an alkyl group having from 14 to 25 carbon atoms.

In the above-described formulae (I) to (XXIII), substituents for the substituted alkoxy group include an alkoxy group, an alkoxyalkoxy group, an alkoxyalkoxyalkoxy group and the like. The substituted aralkyl group includes a benzyl or phenylethyl group substituted with a halogen atom, e.g., a fluorine atom, a chlorine atom, a bromine atom, etc:, an alkyl group or an alkoxy group. The substituted aryl group includes a phenyl group, etc. substituted with the same substituents as enumerated for the substituted aralkyl group. The heterocyclic ring as represented by rings C or C' includes a furan ring, a dihydrofuran ring, a thiophene ring, a dihydrothiophene ring, a pyrrole ring, a dihydropyrrole ring, a pyrazole ring, an imidazole ring, a thiazole ring, a pyridine ring, a dihydropyridine ring, a tetrahydropyridine ring, a pyridazine ring, a pyrimidine ring, a pyrazine ring, a thiapyran ring, a quinoxaline ring, etc.

In the above-described formula (VIII), at least one of $R^{10}$, $R^{13}$ and $R^{14}$ is an alkyl group having from 1 to 13 carbon atoms or a substituted or unsubstituted alkoxy group having from 1 to 13 carbon atoms as mentioned above. When all of $R^{10}$, $R^{13}$ and $R^{14}$ are hydrogen atoms in the formula (VIII), such compounds are limited in application because they are sparingly soluble in the hereinafter described solvents and also show the maximum absorption at 814 nm (in chloroform) that is far aside from the oscillation wavelength of semiconductor lasers, i.e., 780 nm, 830 nm or 850 nm.

In the above-described formula (IX), at least one of the pairs of the symmetrically positioned substituents, i.e., $R^6$ and $R^{6'}$; $R^{22}$ and $R^{22'}$; $R^{23}$ and $R^{23'}$; and $R^{24}$ and $R^{24'}$, comprises different groups. If each of all these pairs comprises the same groups, such compounds may become sparingly soluble in the solvents hereinafter described and, therefore, find a limited application.

The compounds (I) of the present invention are soluble in halogen-containing hydrocarbon solvents, e.g., chloroform, dichloromethane, dichloroethane, etc.; ether solvents, e.g., diethyl ether, dioxane, tetrahydrofuran, dimethoxyethane, etc.; ester solvents, e.g., ethyl acetate, etc.; aromatic hydrocarbon solvents, e.g., benzene, toluene, xylene, chlorobenzenes, etc.; amide solvents, e.g., acetamide, N,N-dimethylacetamide, N-methylpyrrolidone, etc.; alcohol solvents, e.g., methanol, ethanol, methyl cellosolve, etc.; dimethyl sulfoxide; and the like. They also exhibit satisfactory light-resistance.

In addition to the solubility in a wide variety of solvents and good light-resistance as described above, the compounds of the present invention possess a remarkable industrial value in that the maximum absorption wavelengths in the above-recited solvents fall within a range of from 700 to 900 nm and, in particular, are centered mainly in the vicinity of 780 nm, 830 nm or 850 nm that is an oscillation wavelength of a semiconductor laser. Therefore, they are expected to be useful in the field of various information materials utilizing a laser beam, such as laser beam-absorbing materials for laser recording liquid crystal display devices, electrophotographic light-sensitive materials of electrophotographic printers using a laser beam as a light source, recording materials for photodiscs in which an information can be recorded and read-out by a laser beam, infrared-cut filters, and the like.

The squarilium compounds of the present invention can also be employed in liquid crystal compositions in combination with liquid crystals for the above-described liquid crystal display devices in which an information is recorded by a laser beam.

The liquid crystals which can be used in combination with the squarilium compounds of this invention include smectic liquid crystals and cholesteric liquid crystals.

Examples of the smectic liquid crystals are biphenyl type liquid crystals, terphenyl type liquid crystals, cyclohexylcyclohexane type liquid crystals, biphenylcyclohexane type liquid crystals, cyclohexylbiphenylcyclohexane type liquid crystals, phenylcyclohexyl carboxylate type liquid crystals, cyclohexylcyclohexyl benzoate type liquid crystals, cyclohexylphenylcyclohexyl carboxylate type liquid crystals, cyclohexylcyclohexylcyclohexyl carboxylate type liquid crystals, pyrimidine type liquid crystals, etc. and mixtures thereof Cholesteric liquid crystals can be obtained by adding an optically active substance to nematic liquid crystals of, for example, cyclohexylcyclohexane type liquid crystals, phenylcyclohexane type liquid crystals, biphenyl type liquid crystals, terphenyl type liquid crystals, phenylcyclohexyl carboxylate type liquid crystals, phenyl benzoate type liquid crystals, etc.

The optically active substance to be used includes chiralnematic compounds wherein an optically active group, e.g., a 2-methylbutyl group, a 3-methylbutoxy group, a 3-methylpentyl group, a 3-methylpentoxy group, a 4-methylhexyl group, a 4-methylhexyloxy group, etc., is introduced to a nematic liquid crystals. Additional examples of the optically active substance include derivatives of alcohols, e.g., l-menthol, d-borneol, etc.; derivatives of d-camphor, 3-methylcyclohexane, etc.; derivatives of carboxylic acids, e.g., d-citronellic acid, l-camphoric acid, etc.; derivatives of aldehydes, e.g., d-citronellal, etc.; derivatives of alkenes, e.g., d-linonene, etc.; derivatives of amines, amides or nitriles; and the like.

The liquid crystal compositions in accordance with the present invention can contain known dichromic dyes and additives, such as viscosity reducing agent.

The present invention will now be illustrated in greater detail with reference to the following examples, but it should be understood that these examples are not limiting the present invention.

EXAMPLE 1

To 0.11 g of 3,4-dihydroxy-3-cyclobutene-1,2-dione was added 15 ml of n-butyl alcohol, and the mixture was heated to about 100° C. to form a solution. To this solution were added 0.46 g of 1-n-propyl-5-isopropylazulene and 10 ml of benzene, and the mixture was stirred at 95° to 105° C. for about 1 hour while azeotropically removing the produced water. After cooling, n-hexane was added thereto, and the precipitated crystals were purified by column chromatography to obtain a squarilium compound having the formula:

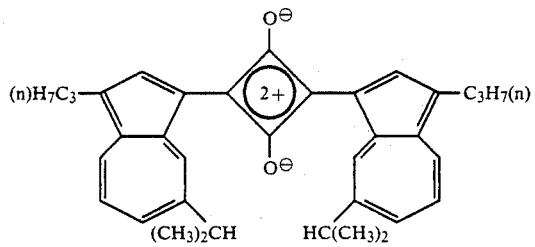

This compound had a melting point of 241.0° to 243.0° C., and its visible absorption spectrum in a chloroform solution had a maximum absorption wavelength of 726 nm.

The resulting compound was added to cyanooctylbiphenyl (a biphenyl type liquid crystal having a smectic phase) at a ratio of 0.5% by weight, followed by stirring under heating at 50° C. or higher to thereby form an isotropic liquid showing a maximum absorption spectrum at 739 nm.

The thus prepared liquid (liquid crystal composition) was sealed in an element composed of upper and lower glass plates with a gap therebetween being 9 μm, in which each of the surfaces having a transparent electrode and contacting the liquid crystal had been subjected to vertical orientation treatment with a vertically orientating agent, octadecyldimethyl[3-(trimethoxysilyl)propyl]ammonium chloride. The element was irradiated with a GaAlAs semiconductor laser having an oscillation wavelength at 780 nm in a spot of 10 μm. The irradiated spot got a rise in temperature, and the liquid crystal portion corresponding to the spot wherein molecules had been regularly oriented in a vertical direction turned into an isotropic liquid. The irradiation of a laser beam was interrupted, and the element was cooled. When a halogen lamp light was transmitted through the element and projected on a screen to obtain a 10-fold enlarged projective figure, a black and highly contrast figure was obtained on the screen through the liquid crystal portion where the orientation of the liquid crystal molecules was disturbed.

EXAMPLE 2

In the same manner as described in Example 1, a squarilium compound of the formula:

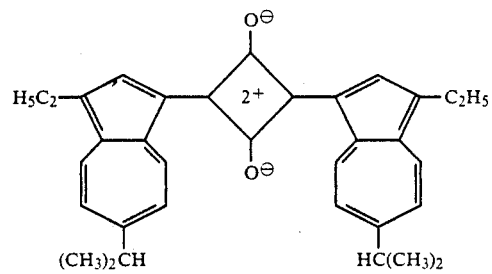

was prepared This compound had a melting point of 266.5° to 267.0° C. and its absorption spectrum in chloroform showed its maximum peak at 732 nm.

The resulting compound was added to a 1:1 mixture of cyanooctylbiphenyl and cyanononylbiphenyl in an amount of 0.5% by weight, followed by stirring under heating at 50° C. or higher to thereby form an isotropic liquid having its maximum absorption peak at 740 nm.

Display was carried out in the same manner as described in Example 1 but using the resulting isotropic liquid. There was obtained a projected figure having satisfactory contrast.

EXAMPLES 3 TO 21

In the same manner as described in Example 1, squarilium compounds shown in Table 1 below were prepared, and an isotropic liquid was prepared from each of the resulting compounds in the same manner as in Example 1. A maximum absorption wavelength of the isotropic liquid in chloroform ($\lambda_{max}$) is shown in Table 1 below.

TABLE 1

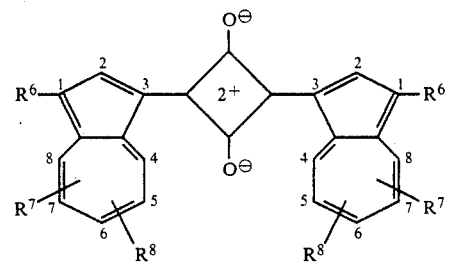

| Example No. | $-R^6$ | (position)-$R^7$ | (position)-$R^8$ | $\lambda_{max}$ (nm) |
|---|---|---|---|---|
| 3 | $-CH_3$ | (5)-$CH(CH_3)_2$ | $-H$ | 738 |
| 4 | $-C_2H_5$ | (5)-$CH(CH_3)_2$ | $-H$ | 739 |
| 5 | $-C_3H_7(n)$ | (5)-$CH(CH_3)_2$ | $-H$ | 739 |
| 6 | $-CH(CH_3)_2$ | (5)-$CH(CH_3)_2$ | $-H$ | 738 |
| 7 | $-C_4H_9(n)$ | (5)-$CH(CH_3)_2$ | $-H$ | 739 |
| 8 | $-C_5H_{11}(n)$ | (5)-$CH(CH_3)_2$ | $-H$ | 740 |
| 9 | $-C_6H_{13}(n)$ | (5)-$CH(CH_3)_2$ | $-H$ | 740 |
| 10 | $-C_7H_{15}(n)$ | (5)-$CH(CH_3)_2$ | $-H$ | 740 |
| 11 | $-C_8H_{17}(n)$ | (5)-$CH(CH_3)_2$ | $-H$ | 741 |
| 12 | $-CH_3$ | (6)-$CH(CH_3)_2$ | $-H$ | 740 |
| 13 | $-C_2H_5$ | (6)-$CH(CH_3)_2$ | $-H$ | 740 |
| 14 | $-C_3H_7(n)$ | (6)-$CH(CH_3)_2$ | $-H$ | 740 |
| 15 | $-C_8H_{17}(n)$ | (6)-$CH(CH_3)_2$ | $-H$ | 741 |
| 16 | $-CH_3$ | (8)-$OCH_3$ | $-H$ | 752 |
| 17 | $-C_2H_5$ | (8)-$OCH_3$ | $-H$ | 752 |
| 18 | $-C_5H_{11}(n)$ | (8)-$OCH_3$ | $-H$ | 753 |
| 19 | $-C_8H_{17}(n)$ | (8)-$OCH_3$ | $-H$ | 753 |
| 20 | $-CH_3$ | (5)-$CH_3$ | (8)-$CH_3$ | 758 |

TABLE 1-continued

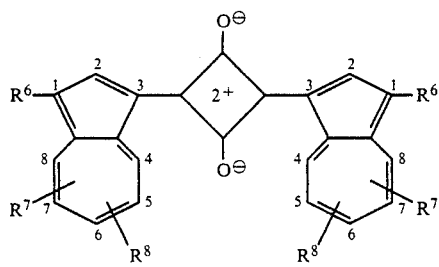

| Example No. | —R⁶ | (position)-R⁷ | (position)-R⁸ | λmax (nm) |
|---|---|---|---|---|
| 21 | —CH₃ | (6)-CH₃ | (8)-CH₃ | 756 |

EXAMPLE 22

To 0.15 g of 3,4-dihydroxy-3-cyclobutene-1,2-dione was added 15 ml of n-butyl alcohol, and the mixture was heated to about 100° C. to form a solution. To this solution were added 0.65 g (0.0026 mol) of 1-phenyl-5-isopropylazulene and 10 ml of benzene, and the mixture was heated at 95° to 105° C. for about 1 hour with stirring while azeotropically removing the produced water.

The reaction mixture was cooled, and n-hexane was added thereto. The precipitated crystals were purified by column chromatography to obtain 0.13 g of a compound of the formula:

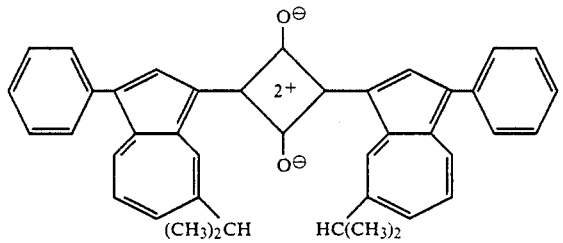

This compound had a melting point of 286.0° to 287.0° C. and its visible absorption spectrum in a chloroform solution had a maximum absorption wavelength of 747 nm.

The resulting compound was dissolved in a cyanobiphenyl type liquid crystal in a concentration of 0.30% by weight. When the solution was subjected to light resistance test by ultraviolet irradiation using a black light ("FL-20SBLB" manufactured by Toshiba Electric Corp.), it was stable even after 15-hour-irradiation.

EXAMPLE 23

In the same manner as described in Example 22 but replacing the 1-phenyl-5-isopropylazulene as used in Example 22 with the equimolar amount (0.68 g) of 1-benzyl-5-isopropylazulene, 0.65 g of a compound having the following formula was obtained:

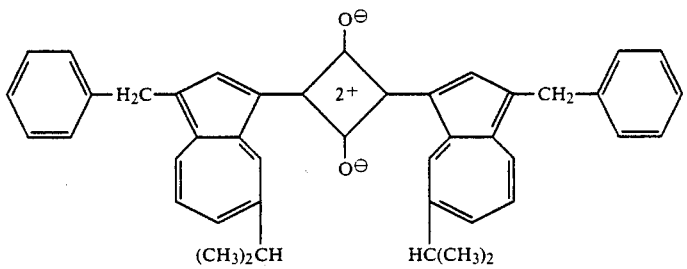

This compound exhibited satisfactory light resistance in the same light resistance test as in Example 22.

EXAMPLES 24 TO 41

Compounds shown in Table 2 were prepared in the same manner as described in Example 22 except for replacing the 1-phenyl-5-isopropylazulene as used in Example 22 with azulene compounds correspondingly having the same substituents as possessed by the compounds shown in Table 2.

The maximum absorption wavelengths of visible absorption spectra of these compounds in their chloroform solutions are shown in Table 2.

TABLE 2

| Example No. | —R⁹ | (position)-R¹⁰ | λmax (nm) |
|---|---|---|---|
| 24 | phenyl | (5)-CH₃ | 746 |
| 25 | phenyl | —H | 733 |
| 26 | phenyl | (6)-CH(CH₃)₂ | 751 |
| 27 | m-tolyl (CH₃) | (5)-CH(CH₃)₂ | 746 |

TABLE 2-continued

| Example No. | —R⁹ | (position)-R¹⁰ | $\lambda_{max}$ (nm) |
|---|---|---|---|
| 28 | —C₆H₄—OC₄H₉(n) | (5)-CH(CH₃)₂ | 755 |
| 29 | —C₆H₄—C₄H₉(n) | (5)-CH(CH₃)₂ | 747 |
| 30 | —C₆H₄—C₇H₁₅(n) | (5)-CH(CH₃)₂ | 747 |
| 31 | —C₆H₄—C₈H₁₇(n) | (5)-CH(CH₃)₂ | 747 |
| 32 | —C₆H₄—Cl | (6)-CH(CH₃)₂ | 750 |
| 33 | —CH₂—C₆H₅ | (5)-CH₃ | 724 |
| 34 | —CH₂—C₆H₄—Br | (6)-CH₃ | 729 |
| 35 | —CH₂—C₆H₅ | (6)-CH(CH₃)₂ | 729 |
| 36 | —CH₂—C₆H₄—CH₃ | (5)-CH(CH₃)₂ | 725 |
| 37 | —CH₂—C₆H₄—C₄H₉(n) | (5)-CH(CH₃)₂ | 725 |
| 38 | —CH₂—C₆H₄—OC₆H₁₃(n) | (5)-CH(CH₃)₂ | 726 |
| 39 | —CH₂—C₆H₄—C₈H₁₇(n) | (6)-CH(CH₃)₂ | 730 |
| 40 | —CH₂—CH₂—C₆H₅ | (5)-CH(CH₃)₂ | 725 |
| 41 | naphthyl | (5)-CH(CH₃)₂ | 756 |

EXAMPLE 42

To 0.12 g of 3,4-dihydroxy-3-cyclobutene-1,2-dione was added 15 ml of n-butyl alcohol, and the mixture was heated to about 100° C. to form a solution. To the solution were added 0.43 g of 1,2-trimethylene-5-isopropylazulene and 10 ml of benzene, and the resulting mixture was heated to 95° to 105° C. for about 1 hour under stirring while azeotropically removing the produced water.

After cooling, n-hexane was added to the reaction mixture, and the precipitated crystals were purified column chromatography to obtain a compound of the formula:

This compound had a melting point of 269.0° to 270.0° C. and its visible absorption spectrum in a chloroform solution had a maximum absorption wavelength of 742 nm.

The compound exhibited stability in the same light resistance test as in Example 22.

EXAMPLES 43 TO 56

Compounds shown in Tables 3 and 4 were prepared in the same manner as described in Example 42 except for replacing the 1,2-trimethylene-5-isopropylazulene with corresponding azulene compounds having the same substituents as in the compounds of Tables 3 and 4, respectively.

The maximum absorption wavelengths of visible absorption spectra of these compounds in their chloroform solutions are shown in Tables 3 and 4, respectively.

TABLE 3

| Example No. | —R¹² | —R¹¹ | (position)-R¹⁰ | $\lambda_{max}$ (nm) |
|---|---|---|---|---|
| 43 | $-C_2H_5$ | $-CH_3$ | (5)-$CH(CH_3)_2$ | 758 |
| 44 | $-C_3H_7(n)$ | $-C_2H_5$ | (5)-$CH(CH_3)_2$ | 758 |
| 45 | $-C_4H_9(n)$ | $-C_3H_7(n)$ | (5)-$CH(CH_3)_2$ | 758 |
| 46 | $-C_5H_{11}(n)$ | $-C_4H_9(n)$ | (5)-$CH(CH_3)_2$ | 758 |
| 47 | $-C_6H_{13}(n)$ | $-C_5H_{11}(n)$ | (6)-$CH(CH_3)_2$ | 763 |
| 48 | $-C_8H_{17}(n)$ | $-C_7H_{15}(n)$ | (6)-$CH(CH_3)_2$ | 763 |
| 49 | $-C_{11}H_{23}(n)$ | $-C_{10}H_{21}(n)$ | (5)-$CH(CH_3)_2$ | 763 |
| 50 | $-C_{13}H_{27}(n)$ | $-C_{12}H_{25}(n)$ | (5)-$CH(CH_3)_2$ | 763 |

TABLE 4

| Example No. | 1,2-Alkylene Group for Forming Ring A | (position)-R¹⁰ | $\lambda_{max}$ (nm) |
|---|---|---|---|
| 51 | $-(CH_2)_3-$ | (5)-$CH_3$ | 742 |
| 52 | $-(CH_2)_3-$ | (6)-$CH(CH_3)_2$ | 745 |
| 53 | $-(CH_2)_4-$ | —H | 742 |
| 54 | $-(CH_2)_4-$ | (5)-$CH_3$ | 758 |
| 55 | $-(CH_2)_2CH-CH_2-$<br>　　　　\|<br>　　　$C_4H_9(tert)$ | (5)-$CH(CH_3)_2$ | 758 |
| 56 | $-(CH_2)_4-$ | (6)-$CH(CH_3)_2$ | 761 |

EXAMPLE 57

To 0.038 g of 3,4-dihydroxy-3-cyclobutene-1,2-dione was added 20 ml of n-butyl alcohol, and the mixture was heated to about 100° C. to form a solution. To the solution were added 0.15 g of 8-isopropyl-benz[a]azulene and 15 ml of benzene, and the mixture was stirred at 95 to 105° C. for about 1 hour while azeotropically removing the produced water. After cooling, n-hexane was added to the reaction mixture, and the precipitated crystals were purified by column chromatography to obtain 0.16 g of a compound of the formula:

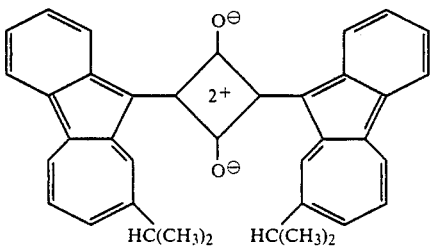

This compound had a melting point of 194° to 195° C., and its absorption spectrum in a chloroform solution showed the maximum absorption at 823 nm.

EXAMPLE 58

In the same manner as described in Example 57 except for replacing the 8-isopropyl-benz[a]azulene as used in Example 57 with the equimolar amount of 3-ethyl-8-isopropyl-benz[a]azulene, a compound of the formula:

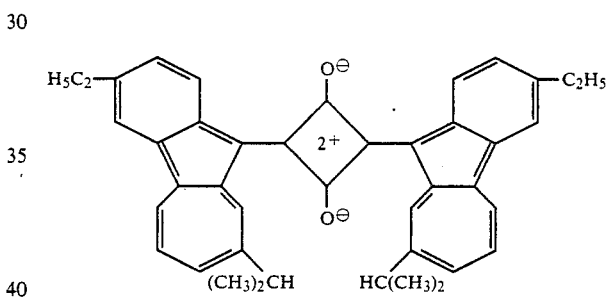

was obtained. This compound had a melting point of to 196° C., and its absorption spectrum in a chloroform solution had the maximum absorption wavelength at 836 nm.

EXAMPLE 59

In the same manner as described in Example 57 except for replacing the 8-isopropyl-benz[a]azulene as used in Example 57 with the equimolar amount of 3-t-butyl-benz[a]azulene and recrystallizing the crude crystals from n-butanol, a compound of the formula:

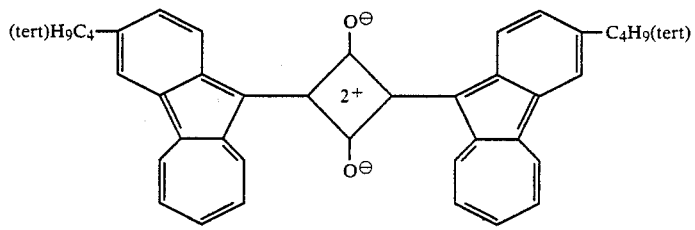

was obtained This compound had a melting point of 310° to 311° C., and its absorption spectrum in a chloroform solution showed the maximum absorption wavelength of 823 nm.

EXAMPLES 60 to 86

In the same manner as described in Example 57, 27 squarilium compounds as shown in Table 5 below were prepared. Structures and maximum absorption wavelengths in chloroform solutions of these compounds are also shown in Table 5.

TABLE 5

| Example No. | (position)-$R^{14}$ | (position)-$R^{13}$ | (position)-$R^{10}$ | $\lambda_{max}$ (nm) |
|---|---|---|---|---|
| 60 | (3)-$C_3H_7$(n) | —H | (8)-$C_3H_7$(iso) | 836 |
| 61 | (3)-$C_4H_9$(n) | —H | (8)-$C_3H_7$(iso) | 836 |
| 62 | (3)-$C_5H_{11}$(n) | —H | (8)-$C_3H_7$(iso) | 836 |
| 63 | (3)-$C_6H_{13}$(n) | —H | (7)-$C_3H_7$(iso) | 841 |
| 64 | (3)-$C_7H_{15}$(n) | —H | (8)-$CH_3$ | 836 |
| 65 | (3)-$C_7H_{15}$(n) | —H | (7)-$CH_3$ | 841 |
| 66 | (3)-$C_7H_{15}$(n) | —H | (8)-$C_3H_7$(iso) | 836 |
| 67 | (3)-$C_8H_{17}$(n) | —H | (8)-$CH_3$ | 836 |
| 68 | (3)-$C_{13}H_{27}$(n) | —H | (8)-$CH_3$ | 836 |
| 69 | (2)-$OCH_3$ | —H | (8)-$C_3H_7$(iso) | 839 |
| 70 | (2)-$OC_4H_9$(n) | —H | (8)-$C_3H_7$(iso) | 839 |
| 71 | (2)-$OC_7H_{15}$(n) | —H | (8)-$CH_3$ | 839 |
| 72 | (3)-$OCH_3$ | —H | (7)-$C_3H_7$(iso) | 847 |
| 73 | (3)-$OCH_3$ | —H | (8)-$C_3H_7$(iso) | 843 |
| 74 | (3)-Br | —H | (8)-$C_3H_7$(iso) | 835 |
| 75 | (3)-$C_2H_5$ | (5)-$OCH_3$ | (8)-$C_3H_7$(iso) | 839 |
| 76 | (3)-$C_4H_9$(tert) | (5)-$OCH_3$ | (8)-$C_3H_7$(iso) | 839 |
| 77 | (3)-$C_4H_9$(n) | (5)-$OCH_3$ | (8)-$C_3H_7$(iso) | 839 |
| 78 | (3)-$C_2H_5$ | (5)-$OC_4H_9$(n) | (8)-$C_3H_7$(iso) | 839 |
| 79 | (3)-$C_3H_7$(n) | (5)-$OC_8H_{17}$(n) | (7)-$C_3H_7$(iso) | 844 |
| 80 | —H | (5)-$OC_{13}H_{27}$(n) | (8)-$C_3H_7$(iso) | 826 |
| 81 | (2)-$OC_2H_4OCH_3$ | —H | (8)-$C_3H_7$(iso) | 839 |
| 82 | (2)-$O(C_2H_4O)_2C_2H_5$ | —H | (8)-$C_3H_7$(iso) | 839 |
| 83 | —H | (5)-$OC_2H_4OC_2H_5$ | (8)-$C_3H_7$(iso) | 826 |
| 84 | —H | (5)-$O(C_2H_4O)_2CH_3$ | (8)-$C_3H_7$(iso) | 826 |
| 85 | (3)-$C_5H_{11}$(n) | —H | —H | 823 |
| 86 | (3)-$C_7H_{15}$(n) | —H | —H | 823 |

EXAMPLE 87

To 0.11 g of 3,4-dihydroxy-3-cyclobutene-1,2-dione was added 30 ml of n-butyl alcohol, and the mixture was heated to about 100° C. to form a solution. To this solution were added 0.20 g of 1-methyl-4-methyl-7-isopropylazulene, 0.23 g of 1-n-butyl-5-isopropylazulene and 20 ml of benzene, and the resulting solution was stirred at 95° to 105° C. for about 1 hour while azeotropically removing the produced water. After cooling, the reaction solution was subjected to column chromatography to obtain 0.01 g of a compound of the formula:

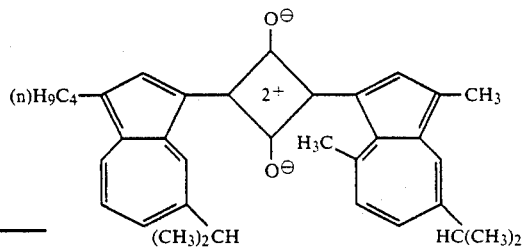

This compound had a melting point of 105.0° to 107.0° C., and the maximum absorption wavelength of its absorption spectrum in a chloroform solution was 755 nm.

EXAMPLE 88

In the same manner as described in Example 87 but replacing the 1-n-butyl-5-isopropylazulene as used in Example 87 with the equimolar amount of 8-isopropyl-benz[a]azulene, a compound of the following formula was obtained:

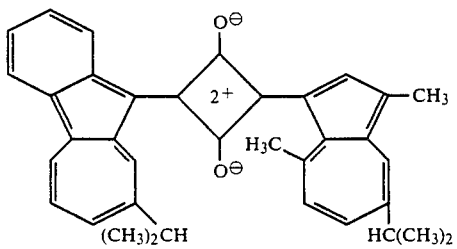

This compound had a melting point of 129.0° to 130.0° C., and the maximum absorption wavelength of its absorption spectrum in a chloroform solution was 796 nm.

EXAMPLES 89 TO 147

In the same manner as described in Example 87, squarilium compounds as shown in Tables 6 to 10 were prepared. Structures and maximum absorption wavelengths in chloroform solutions of these compounds are also shown in Tables 6 to 10 below.

TABLE 6

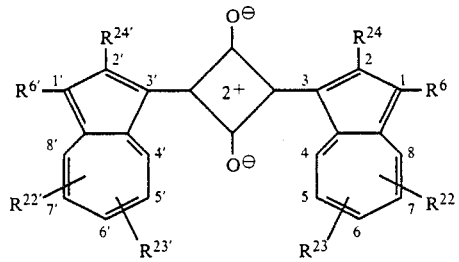

| Example No. | $-R^{24}$ | $-R^6$ | (position)-$R^{22}$ | (position)-$R^{23}$ | $-R^{24'}$ | $-R^{6'}$ | (position)-$R^{22'}$ | (position)-$R^{23'}$ | $\lambda_{max}$ (nm) |
|---|---|---|---|---|---|---|---|---|---|
| 89 | $-H$ | $-CH_3$ | (4)-$CH_3$ | (7)-$C_3H_7$ | $-C_2H_5$ | $-CH_3$ | (5')-$C_3H_7$(iso) | $-H$ | 763 |
| 90 | $-H$ | $-CH_3$ | (4)-$CH_3$ | (7)-$C_3H_7$ | $-C_3H_7$(n) | $-C_2H_5$ | (5')-$C_3H_7$(iso) | $-H$ | 763 |
| 91 | $-H$ | $-CH_3$ | (4)-$CH_3$ | (7)-$C_3H_7$ | $-C_4H_9$(n) | $-C_3H_7$(n) | (5')-$C_3H_7$(iso) | $-H$ | 763 |
| 92 | $-H$ | $-CH_3$ | (4)-$CH_3$ | (7)-$C_3H_7$ | $-C_5H_{11}$(n) | $-C_4H_9$(n) | (5')-$C_3H_7$(iso) | $-H$ | 763 |
| 93 | $-H$ | $-CH_3$ | (4)-$CH_3$ | (7)-$C_3H_7$ | $-C_6H_{13}$(n) | $-C_5H_{11}$(n) | (6')-$C_3H_7$(iso) | $-H$ | 766 |
| 94 | $-H$ | $-CH_3$ | (4)-$CH_3$ | (7)-$C_3H_7$ | $-C_8H_{17}$(n) | $-C_7H_{15}$(n) | (5')-$C_3H_7$(iso) | $-H$ | 766 |
| 95 | $-H$ | $-CH_3$ | (4)-$CH_3$ | (7)-$C_3H_7$ | $-C_{11}H_{23}$(n) | $-C_{10}H_{21}$(n) | (5')-$C_3H_7$(iso) | $-H$ | 766 |
| 96 | $-H$ | $-CH_3$ | (4)-$CH_3$ | (7)-$C_3H_7$ | $-C_{13}H_{27}$(n) | $-C_{12}H_{25}$(n) | (5')-$C_3H_7$(iso) | $-H$ | 766 |
| 97 | $-H$ | $-CH_3$ | (5)-$CH_3$ | (8)-$CH_3$ | $-C_2H_5$ | $-CH_3$ | (5')-$C_3H_7$(iso) | $-H$ | 758 |
| 98 | $-H$ | $-CH_3$ | (6)-$CH_3$ | (8)-$CH_3$ | $-C_3H_7$(n) | $-C_2H_5$ | (5')-$C_3H_7$(iso) | $-H$ | 757 |
| 99 | $-H$ | $-CH_3$ | (6)-$C_3H_7$(iso) | $-H$ | $-C_4H_9$(n) | $-C_3H_7$(n) | (5')-$C_3H_7$(iso) | $-H$ | 749 |
| 100 | $-H$ | $-C_2H_5$ | (6)-$C_3H_7$(iso) | $-H$ | $-C_5H_{11}$(n) | $-C_4H_9$(n) | (5')-$C_3H_7$(iso) | $-H$ | 749 |
| 101 | $-H$ | $-C_3H_7$(n) | (6)-$C_3H_7$(iso) | $-H$ | $-C_6H_{13}$(n) | $-C_5H_{11}$(n) | (6')-$C_3H_7$(iso) | $-H$ | 752 |

TABLE 7

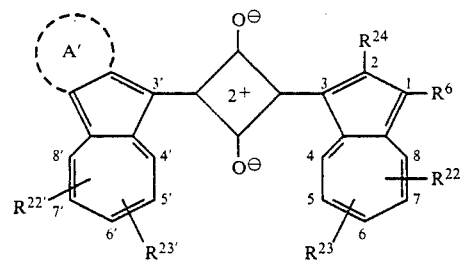

| Example No. | $-R^{24}$ | $-R^6$ | (position)-$R^{22}$ | (position)-$R^{23}$ | 1',2'-Alkylene Group for Forming Ring A' | (position)-$R^{22'}$ | (position)-$R^{23'}$ | $\lambda_{max}$ (nm) |
|---|---|---|---|---|---|---|---|---|
| 102 | $-H$ | $-CH_3$ | (4)-$CH_3$ | (7)-$C_3H_7$ | $+CH_2\!\!\rightarrow_3$ | (5')-$CH_3$ | $-H$ | 755 |
| 103 | $-H$ | $-CH_3$ | (4)-$CH_3$ | (7)-$C_3H_7$ | $+CH_2\!\!\rightarrow_3$ | (6')-$C_3H_7$(iso) | $-H$ | 757 |
| 104 | $-H$ | $-CH_3$ | (4)-$CH_3$ | (7)-$C_3H_7$ | $+CH_2\!\!\rightarrow_4$ | $-H$ | $-H$ | 755 |
| 105 | $-H$ | $-CH_3$ | (4)-$CH_3$ | (7)-$C_3H_7$ | $+CH_2\!\!\rightarrow_4$ | (5')-$CH_3$ | $-H$ | 763 |
| 106 | $-H$ | $-CH_3$ | (4)-$CH_3$ | (7)-$C_3H_7$(iso) | $+CH_2\!\!\rightarrow_2 CH-CH_2-$<br>$\quad\quad\quad\quad\|$<br>$\quad\quad\quad C_4H_9$(tert) | (5')-$C_3H_7$(iso) | $-H$ | 763 |
| 107 | $-H$ | $-CH_3$ | (4)-$CH_3$ | (7)-$C_3H_7$(iso) | $+CH_2\!\!\rightarrow_4$ | (6')-$C_3H_7$-(iso) | $-H$ | 765 |

TABLE 8

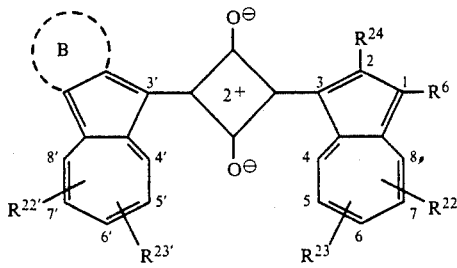

| Example No. | —R$^{24}$ | —R$^6$ | (position)-R$^{22}$ | (position)-R$^{23}$ | 1',2'-Alkylene Group for Forming Ring B | (position)-R$^{22'}$ | (position)-R$^{23'}$ | $\lambda_{max}$ (nm) |
|---|---|---|---|---|---|---|---|---|
| 108 | —H | —CH$_3$ | (4)-CH$_3$ | (7)-C$_3$H$_7$(iso) | —CH=CH—C=CH—<br>　　　　　$\|$<br>　　　　C$_3$H$_7$(n) | (5')-C$_3$H$_7$(iso) | —H | 802 |
| 109 | —H | —CH$_3$ | (4)-CH$_3$ | (7)-C$_3$H$_7$(iso) | —CH=CH—C=CH—<br>　　　　　$\|$<br>　　　　C$_4$H$_9$(n) | (5')-C$_3$H$_7$(iso) | —H | 802 |
| 110 | —H | —CH$_3$ | (4)-CH$_3$ | (7)-C$_3$H$_7$(iso) | —CH=CH—C=CH—<br>　　　　　$\|$<br>　　　　C$_5$H$_{11}$(n) | (5')-C$_3$H$_7$(iso) | —H | 802 |
| 111 | —H | —CH$_3$ | (4)-CH$_3$ | (7)-C$_3$H$_7$(iso) | —CH=CH—C=CH—<br>　　　　　$\|$<br>　　　　C$_6$H$_{13}$(n) | (6')-C$_3$H$_7$(iso) | —H | 805 |
| 112 | —H | —CH$_3$ | (4)-CH$_3$ | (7)-C$_3$H$_7$(iso) | —CH=CH—C=CH—<br>　　　　　$\|$<br>　　　　C$_7$H$_{15}$(n) | (5')-CH$_3$ | —H | 802 |
| 113 | —H | —CH$_3$ | (4)-CH$_3$ | (7)-C$_3$H$_7$(iso) | —CH=CH—C=CH—<br>　　　　　$\|$<br>　　　　C$_7$H$_{15}$(n) | (6')-CH$_3$ | —H | 805 |
| 114 | —H | —CH$_3$ | (4)-CH$_3$ | (7)-C$_3$H$_7$(iso) | —CH=CH—C=CH—<br>　　　　　$\|$<br>　　　　C$_7$H$_{15}$(n) | (5')-C$_3$H$_7$(iso) | —H | 802 |
| 115 | —H | —CH$_3$ | (4)-CH$_3$ | (7)-C$_3$H$_7$(iso) | —CH=CH—C=CH—<br>　　　　　$\|$<br>　　　　C$_8$H$_{17}$(n) | (5')-CH$_3$ | —H | 802 |
| 116 | —H | —CH$_3$ | (4)-CH$_3$ | (7)-C$_3$H$_7$(iso) | —CH=CH—C=CH—<br>　　　　　$\|$<br>　　　　C$_{13}$H$_{27}$(n) | (5')-CH$_3$ | —H | 802 |
| 117 | —H | —CH$_3$ | (4)-CH$_3$ | (7)-C$_3$H$_7$(iso) | —CH=C—CH=CH—<br>　　　$\|$<br>　　OCH$_3$ | (5')-C$_3$H$_7$(iso) | —H | 804 |
| 118 | —H | —CH$_3$ | (4)-CH$_3$ | (7)-C$_3$H$_7$(iso) | —CH=C—CH=CH—<br>　　　$\|$<br>　　OC$_4$H$_9$(n) | (5')-C$_3$H$_7$(iso) | —H | 804 |
| 119 | —H | —CH$_3$ | (8)-OCH$_3$ | —H | —CH=C—CH=CH—<br>　　　$\|$<br>　　OC$_7$H$_{15}$(n) | (5')-CH$_3$ | —H | 796 |
| 120 | —H | —C$_2$H$_5$ | (8)-OCH$_3$ | —H | —CH=CH—C=CH—<br>　　　　　$\|$<br>　　　　OCH$_3$ | (6')-C$_3$H$_7$(iso) | —H | 800 |
| 121 | —H | —C$_5$H$_{11}$(n) | (8)-OCH$_3$ | —H | —CH=CH—C=CH—<br>　　　　　$\|$<br>　　　　OCH$_3$ | (5')-C$_3$H$_7$(iso) | —H | 798 |
| 122 | —H | —C$_8$H$_{17}$(n) | (8)-OCH$_3$ | —H | —CH=CH—C=CH—<br>　　　　　$\|$<br>　　　　Br | (5')-C$_3$H$_7$(iso) | —H | 794 |
| 123 | —H | —CH$_3$ | (5)-C$_3$H$_7$(iso) | —H | —CH=CH—CH=CH— | (8')-OC$_{13}$H$_{27}$(n) | (5')-C$_3$H$_7$(iso) | 782 |

TABLE 8-continued

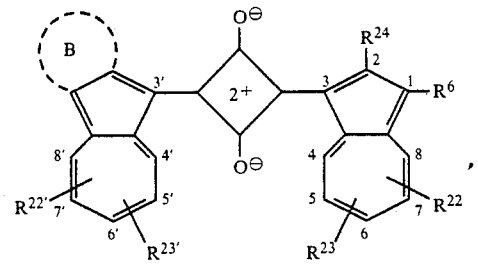

| Example No. | —R²⁴ | —R⁶ | (position)-R²² | (position)-R²³ | 1',2'-Alkylene Group for Forming Ring B | (position)-R²²' | (position)-R²³' | $\lambda_{max}$ (nm) |
|---|---|---|---|---|---|---|---|---|
| 124 | —H | —C₂H₅ | (5)-C₃H₇(iso) | —H | —CH=C—CH=CH—<br>  \|<br>  OC₂H₄OCH₃ | (5')-C₃H₇(iso) | —H | 789 |
| 125 | —H | —C₃H₇(iso) | (5)-C₃H₇(iso) | —H | —CH=C—CH=CH—<br>  \|<br>  O(C₂H₄O)₂C₂H₅ | (5')-C₃H₇(iso) | —H | 789 |
| 126 | —H | —C₅H₁₁(n) | (5)-C₃H₇(iso) | —H | —CH=CH—CH=CH— | (8')-OC₂H₄OC₂H₅ | (5')-C₃H₇(iso) | 783 |
| 127 | —H | —C₇H₁₅(n) | (5)-C₃H₇(iso) | —H | —CH=CH—CH=CH— | (8')-O(C₂H₄O)₂CH₃ | (5')-C₃H₇(iso) | 783 |
| 128 | —H | —CH₃ | (6)-C₃H₇(iso) | —H | —CH=CH—C=CH—<br>  \|<br>  C₅H₁₁(n) | —H | —H | 782 |
| 129 | —H | —C₂H₅ | (6)-C₃H₇(iso) | —H | —CH=CH—C=CH—<br>  \|<br>  C₇H₁₅(n) | —H | —H | 782 |

TABLE 9

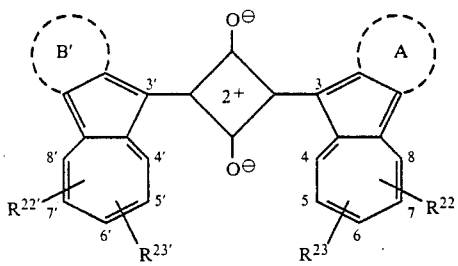

| Example No. | 1,2-Alkylene Group for Forming Ring A | (position)-R²² | (position)-R²³ | 1',2'-Alkylene Group for Forming Ring B' | (position)-R²²' | (position)-R²³' | $\lambda_{max}$ (nm) |
|---|---|---|---|---|---|---|---|
| 130 | ⁺(CH₂)₃ | (5)-CH₃ | —H | —CH=CH—C=CH—<br>  \|<br>  C₂H₅ | (8')-OCH₃ | (5')-C₃H₇(iso) | 791 |
| 131 | ⁺(CH₂)₃ | (6)-C₃H₇(iso) | —H | —CH=CH—C=CH—<br>  \|<br>  C₄H₉(tert) | (8')-OCH₃ | (5')-C₃H₇(iso) | 792 |
| 132 | ⁺(CH₂)₄ | —H | —H | —CH=CH—C=CH—<br>  \|<br>  C₄H₉(n) | (8')-OCH₃ | (5')-C₃H₇(iso) | 791 |
| 133 | ⁺(CH₂)₄ | (5)-CH₃ | —H | —CH=CH—C=CH—<br>  \|<br>  C₂H₅ | (8')-OC₄H₉(n) | (5')-C₃H₇(iso) | 799 |
| 134 | ⁺(CH₂)₄ | (6)-C₃H₇(iso) | —H | —CH=CH—C=CH—<br>  \|<br>  C₃H₇(n) | (8')-OC₈H₁₇(n) | (6')-C₃H₇(iso) | 803 |

TABLE 10

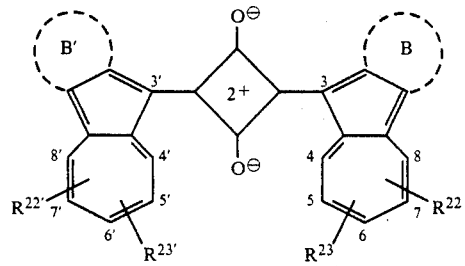

| Example No. | 1,2-Alkylene Group for Forming Ring B | (position)-$R^{22}$ | $-R^{23}$ | 1',2'-Alkylene Group for Forming Ring B' | (position)-$R^{22'}$ | $-R^{23'}$ | $\lambda_{max}$ (nm) |
|---|---|---|---|---|---|---|---|
| 135 | —CH=CH—CH=CH— | —H | —H | —CH=CH—CH=CH— | (5')-$C_3H_7$(iso) | —H | 819 |
| 136 | —CH=CH—C=CH—<br>\|<br>$C_3H_7$(n) | —H | —H | —CH=CH—CH=CH— | (5')-$C_3H_7$(iso) | —H | 823 |
| 137 | —CH=CH—C=CH—<br>\|<br>$C_4H_9$(tert) | —H | —H | —CH=CH—C=CH—<br>\|<br>$C_4H_9$(tert) | (5')-$C_3H_7$(iso) | —H | 830 |
| 138 | —CH=CH—CH=CH— | (5)-$C_3H_7$(iso) | —H | —CH=CH—C=CH—<br>\|<br>$C_2H_5$ | (5')-$C_3H_7$(iso) | —H | 830 |
| 139 | —CH=CH—C=CH—<br>\|<br>$C_5H_{11}$(n) | (5)-$C_3H_7$(iso) | —H | —CH=CH—C=CH—<br>\|<br>$C_2H_5$ | (5')-$C_3H_7$(iso) | —H | 836 |

| Example No. | 1,2-Alkylene Group for Forming Ring B | (position)-$R^{22}$ | (position)-$R^{23}$ | 1',2'-Alkylene Group for Forming Ring B' | (position)-$R^{22'}$ | (position)-$R^{23'}$ | $\lambda_{max}$ (nm) |
|---|---|---|---|---|---|---|---|
| 140 | —CH=CH—C=CH—<br>\|<br>$C_6H_{13}$(n) | —H | —H | —CH=CH—CH=CH— | (6')-$C_3H_7$(iso) | —H | 825 |
| 141 | —CH=CH—C=CH—<br>\|<br>$C_4H_9$(tert) | —H | —H | —CH=CH—C=CH—<br>\|<br>$C_7H_{15}$(n) | (6')-$C_3H_7$(iso) | —H | 833 |
| 142 | —CH=CH—CH=CH— | (5)-$C_3H_7$(iso) | —H | —CH=CH—CH=CH— | (6')-$C_3H_7$(iso) | —H | 826 |
| 143 | —CH=CH—C=CH—<br>\|<br>$C_8H_{17}$(n) | (5)-$C_3H_7$(iso) | —H | —CH=CH—CH=CH— | (6')-$C_3H_7$(iso) | —H | 834 |
| 144 | —CH=CH—CH=CH— | (5)-$C_3H_7$(iso) | —H | —CH=CH—C=CH—<br>\|<br>$C_5H_{11}$(n) | (6')-$C_3H_7$(iso) | —H | 833 |
| 145 | —CH=CH—C=CH—<br>\|<br>$C_3H_7$(n) | (5)-$C_3H_7$(iso) | —H | —CH=CH—C=CH—<br>\|<br>$C_3H_7$(n) | (6')-$C_3H_7$(iso) | —H | 839 |
| 146 | —CH=CH—CH=CH— | (6)-$C_3H_7$(iso) | —H | —CH=CH—C=CH—<br>\|<br>$C_4H_9$(n) | (6')-$C_3H_7$(iso) | —H | 836 |
| 147 | —CH=CH—C=CH—<br>\|<br>$C_2H_5$ | (6)-$C_3H_7$(iso) | —H | —CH=CH—C=CH—<br>\|<br>$C_4H_9$(n) | (6')-$C_3H_7$(iso) | —H | 844 |

EXAMPLE 148

To 0.11 g of 3,4-dihydroxy-3-cyclobutene-1,2-dione was added 30 ml of n-butyl alcohol, and the mixture was heated to about 100° C. to form a solution. To the solution were added 0.20 g of 1,4-dimethyl-7-isopropylazulene, 0.17 g of 4,6,8-trimethylazulene and 20 ml of toluene, and the mixture was stirred at 105° to 110° C. for about 1 hour while azeotropically removing the produced water. After cooling, the reaction mixture was purified by column chromatography to obtain 0.05 g of a compound of the formula:

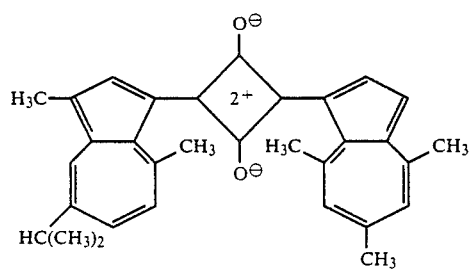

This compound had a melting point of 232° to 233° C., and its absorption spectrum in a chloroform solution showed the maximum absorption at 744 nm.

EXAMPLES 149 TO 180

In the same manner as described in Example 148, squarilium compounds shown in Tables 11 to 13 below were prepared. Their structures and the maximum

TABLE 11

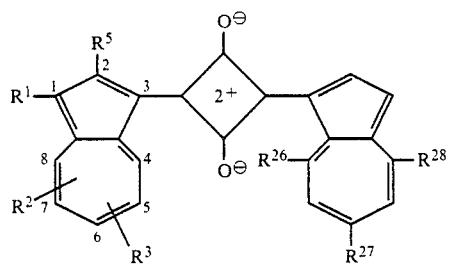

| Example No. | $-R^{28}$ | $-R^{27}$ | $-R^{26}$ | $-R^5$ | $-R^1$ | (position)-$R^2$ | (position)-$R^3$ | $\lambda_{max}$ (nm) |
|---|---|---|---|---|---|---|---|---|
| 149 | $-CH_3$ | $-CH_3$ | $-CH_3$ | $-C_2H_5$ | $-CH_3$ | (5)-$C_3H_7$(iso) | $-H$ | 740 |
| 150 | $-CH_3$ | $-CH_3$ | $-CH_3$ | $-C_3H_7(n)$ | $-C_2H_5$ | (5)-$C_3H_7$(iso) | $-H$ | 740 |
| 151 | $-CH_3$ | $-CH_3$ | $-CH_3$ | $-C_4H_9(n)$ | $-C_3H_7(n)$ | (5)-$C_3H_7$(iso) | $-H$ | 740 |
| 152 | $-CH_3$ | $-CH_3$ | $-CH_3$ | $-C_6H_{13}(n)$ | $-C_5H_{11}(n)$ | (6)-$C_3H_7$(iso) | $-H$ | 743 |
| 153 | $-CH_3$ | $-CH_3$ | $-CH_3$ | $-C_8H_{17}(n)$ | $-C_7H_{15}(n)$ | (6)-$C_3H_7$(iso) | $-H$ | 743 |
| 154 | $-CH_3$ | $-CH_3$ | $-CH_3$ | $-C_5H_{11}(n)$ | $-C_4H_9(n)$ | (5)-$C_3H_7$(iso) | $-H$ | 740 |
| 155 | $-CH_3$ | $-CH_3$ | $-CH_3$ | $-C_{11}H_{23}(n)$ | $-C_{10}H_{21}(n)$ | (5)-$C_3H_7$(iso) | $-H$ | 740 |
| 156 | $-CH_3$ | $-C_3H_7$(iso) | $-CH_3$ | $-C_{13}H_{27}(n)$ | $-C_{12}H_{25}(n)$ | (5)-$C_3H_7$(iso) | $-H$ | 740 |
| 157 | $-CH_3$ | $-CH_3$ | $-CH_3$ | $-H$ | $-CH_3$ | (5)-$C_3H_7$(iso) | $-H$ | 724 |
| 158 | $-CH_3$ | $-CH_3$ | $-CH_3$ | $-H$ | $-C_3H_7(n)$ | (5)-$C_3H_7$(iso) | $-H$ | 724 |
| 159 | $-CH_3$ | $-C_4H_9$(tert) | $-CH_3$ | $-H$ | $-C_8H_{17}(n)$ | (5)-$C_3H_7$(iso) | $-H$ | 725 |
| 160 | $-CH_3$ | $-CH_3$ | $-CH_3$ | $-H$ | $-C_{10}H_{21}(n)$ | (5)-$C_3H_7$(iso) | $-H$ | 724 |
| 161 | $-CH_3$ | $-CH_3$ | $-CH_3$ | $-H$ | $-C_{18}H_{37}(n)$ | (5)-$C_3H_7$(iso) | $-H$ | 724 |
| 162 | $-CH_3$ | $-CH_3$ | $-CH_3$ | $-H$ | $-C_4H_9(n)$ | (8)-$OCH_3$ | (5)-$C_3H_7$(iso) | 726 |
| 163 | $-CH_3$ | $-CH_3$ | $-CH_3$ | $-H$ | $-C_3H_7(n)$ | (8)-$OC_7H_{15}(n)$ | (5)-$C_3H_7$(iso) | 726 |
| 164 | $-CH_3$ | $-CH_3$ | $-CH_3$ | $-H$ | $-C_2H_5(n)$ | (8)-$OC_{18}H_{37}(n)$ | (5)-$C_3H_7$(iso) | 726 |
| 165 | $-CH_3$ | $-CH_3$ | $-CH_3$ | $-H$ | $-C_5H_{11}(n)$ | (8)-$OC_2H_4OC_2H_5$ | (5)-$C_3H_7$(iso) | 726 |
| 166 | $-CH_3$ | $-CH_3$ | $-CH_3$ | $-H$ | ![phenyl with isopropyl] | (5)-$C_3H_7$(iso) | $-H$ | 735 |
| 167 | $-CH_3$ | $-CH_3$ | $-CH_3$ | $-H$ | $-CH_2-$phenyl | (5)-$C_3H_7$(iso) | $-H$ | 723 |
| 168 | $-CH_3$ | $-CH_3$ | $-CH_3$ | $-H$ | $-H$ | $-H$ | $-H$ | 704 |

TABLE 12

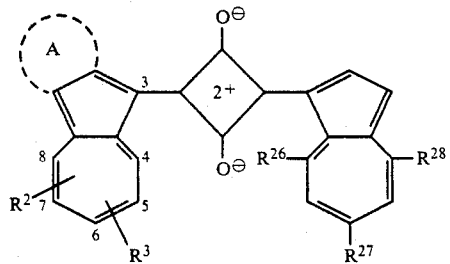

| Example No. | $-R^{28}$ | $-R^{27}$ | $-R^{26}$ | 1,2-Alkylene Group for Forming Ring A | (position)-$R^2$ | (position)-$R^3$ | $\lambda_{max}$ (nm) |
|---|---|---|---|---|---|---|---|
| 169 | $-CH_3$ | $-CH_3$ | $-CH_3$ | $-(CH_2)_3-$ | (5)-$CH_3$ | $-H$ | 732 |
| 170 | $-CH_3$ | $-CH_3$ | $-CH_3$ | $-(CH_2)_3-$ | (6)-$C_3H_7$(iso) | $-H$ | 735 |
| 171 | $-CH_3$ | $-CH_3$ | $-CH_3$ | $-(CH_2)_4-$ | $-H$ | $-H$ | 733 |
| 172 | $-CH_3$ | $-CH_3$ | $-CH_3$ | $-(CH_2)_4-$ | (5)-$CH_3$ | $-H$ | 740 |

TABLE 13

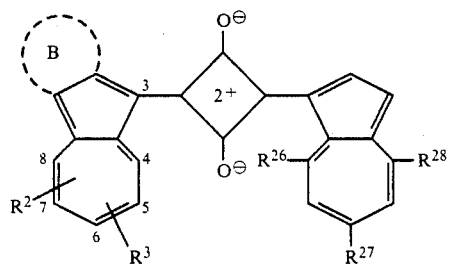

| Example No. | $-R^{28}$ | $-R^{27}$ | $-R^{26}$ | 1,2-Alkylene Group for Forming Ring B | (position)-$R^2$ | (position)-$R^3$ | $\lambda_{max}$ (nm) |
|---|---|---|---|---|---|---|---|
| 173 | $-CH_3$ | $-CH_3$ | $-CH_3$ | $-CH=CH-CH=CH-$ | (5)-$C_3H_7$(iso) | $-H$ | 773 |
| 174 | $-CH_3$ | $-CH_3$ | $-CH_3$ | $-CH=CH-CH=CH-$ | (8)-$(OC_2H_4)_2-OCH_3$ | (5)-$C_3H_7$(iso) | 775 |
| 175 | $-CH_3$ | $-CH_3$ | $-CH_3$ | $-CH=CH-CH=CH-$ | (6)-$C_3H_7$(iso) | $-H$ | 776 |
| 176 | $-CH_3$ | $-CH_3$ | $-CH_3$ | $-CH=CH-C(C_4H_9(tert))=CH-$ | (5)-$C_3H_7$(iso) | $-H$ | 779 |
| 177 | $-CH_3$ | $-CH_3$ | $-CH_3$ | $-CH=CH-C(C_8H_{17}(n))=CH-$ | (5)-$C_3H_7$(iso) | $-H$ | 780 |
| 178 | $-CH_3$ | $-CH_3$ | $-CH_3$ | $-CH=CH-C(OCH_3)=CH-$ | (5)-$C_3H_7$(iso) | $-H$ | 784 |
| 179 | $-CH_3$ | $-CH_3$ | $-CH_3$ | $-CH=C(OCH_3)-CH=CH-$ | (5)-$C_3H_7$(iso) | $-H$ | 782 |
| 180 | $-CH_3$ | $-CH_3$ | $-CH_3$ | $-CH=CH-C(Br)=CH-$ | (5)-$C_3H_7$(iso) | $-H$ | 778 |

EXAMPLE 181

Ten milliliters of n-butyl alcohol was added to 37 mg of 3,4-dihydroxy-3-cyclobutene-1,2-dione, and the mixture was heated to about 100° C. to form a solution. To the solution were added 120 mg of azuleno[1,2-b]thiophene and 15 ml of toluene, and the mixture was stirred at 105 to 110° C. for about 20 minutes while azeotropically removing the produced water. After cooling, the reaction mixture was purified by column chromatography to obtain a compound of the formula:

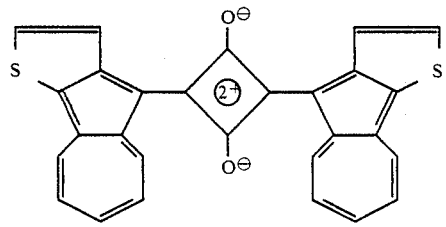

This compound was not melted below 300° C., and its absorption spectrum in the chloroform solution showed the maximum absorption at 775 nm.

EXAMPLE 182

In the same manner as described in Example 181 but replacing the azuleno[1,2-b]thiophene as used in Example 181 with the equimolar amount of 7-isopropylazuleno[1,2-b]thiophene, a compound of the following formula was obtained:

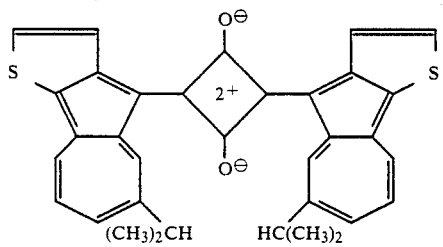

This compound had a melting point of 224.5° to 226.0° C. and the maximum absorption wavelength in its chloroform solution was 783 nm.

EXAMPLE 183

In the same manner as described in Example 181 but replacing the azuleno[1,2-b]thiophene as used in Example 181 with the equimolar amount of 7-isopropylazuleno[1,2-b]1,2-dihydrothiophene, a compound of the following formula was obtained:

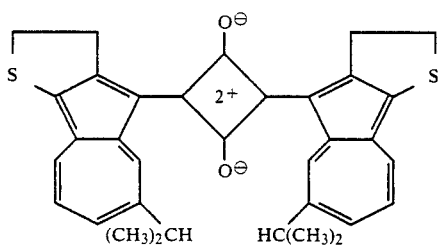

This compound had a melting point of 219.0° to 220.5° C. and its absorption spectrum in a chloroform solution showed the maximum absorption at 815 nm.

EXAMPLE 184

In the same manner as in Example 181 except for replacing the azuleno[1,2-b]thiophene as used in Example 181 with the equimolar amount of 7-isopropylazuleno[1,2-c]-1,3-dihydrothiophene, a compound of the following formula was obtained:

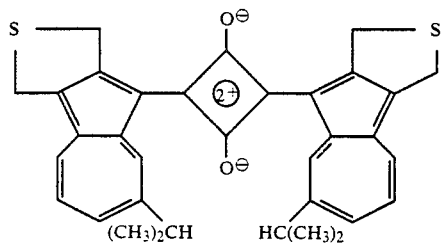

This compound had a melting point of 249.5° to 250.5° C. and its absorption spectrum in the chloroform solution showed the maximum absorption at 746 nm.

EXAMPLE 185

In the same manner as described in Example 181 but replacing the azuleno[1,2-b]thiophene with the equimolar amount of 7-isopropylazuleno[2,1-b]2,3-dihydrothiophene, a compound of the following formula was obtained.

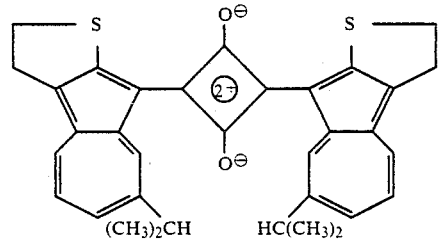

This compound had a melting point of 220.0° to 221.5° C. and its absorption spectrum in the chloroform solution showed the maximum absorption at 815 nm.

EXAMPLE 186

In the same manner as in Example 181 except for replacing the azuleno[1,2-b]thiophene as used in Example 181 with the equimolar amount of 6-isopropylazuleno[1,2-b]1,2-dihydrothiophene, a compound of the following formula was obtained:

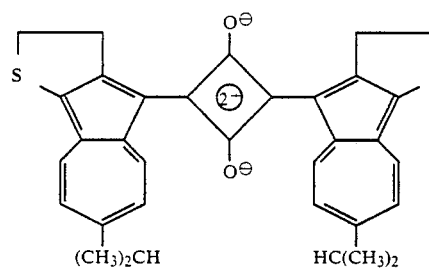

This compound had a melting point of 254.5° to 255.0° C., and its absorption spectrum in the chloroform solution showed the maximum absorption at 804 nm.

EXAMPLE 187

In the same manner as in Example 181 except for replacing the azuleno[1,2-b]thiophene as used in Example 181 with the equimolar amount of 7-isopropylazuleno[1,2-b]furan, a compound of the following formula was obtained:

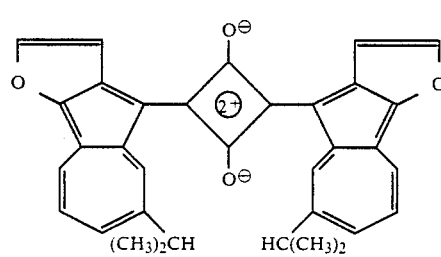

This compound was not melted below 300° C., and its absorption spectrum in the chloroform solution showed the maximum absorption at 760 nm.

EXAMPLE 188

In the same manner as in Example 181 but replacing the azuleno[1,2-b]thiophene with the equimolar amount of 3-ethoxycarbonyl-8-isopropylazuleno[1,2-c]1,2,3,4-tetrahydropyridine, a compound of the following formula was obtained:

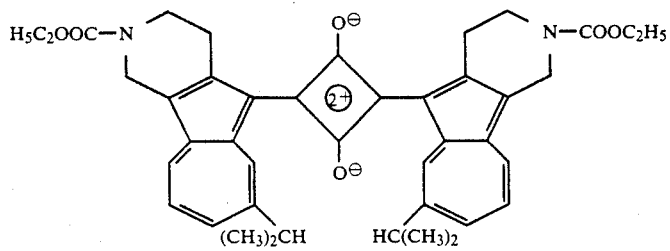

This compound had a melting point of 219° to 220° C., and its absorption spectrum in the chloroform solution showed the maximum absorption at 752 nm.

EXAMPLES 189 TO 263

In the same manner as described in Example 181, squarilium compounds shown in Tables 14 to 17 were obtained. Their structures and the maximum absorption wavelengths in their chloroform solutions are shown in Tables 14 to 17.

TABLE 14

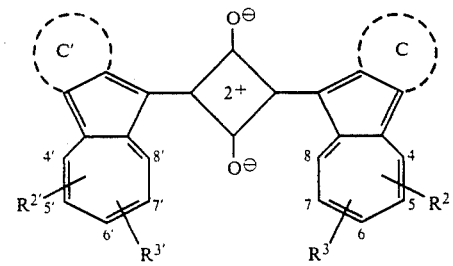

| Example No. | C | (position)-$R^2$ | (position)-$R^3$ | C' | (position)-$R^{2'}$ | (position)-$R^{3'}$ | $\lambda_{max}$ (nm) |
|---|---|---|---|---|---|---|---|
| 189 | (1,2-S3 thiophene ring) | (6)-$C_3H_7$(iso) | —H | (2',1'-3'S thiophene ring) | (6')-$C_3H_7$(iso) | —H | 772 |
| 190 | (S thiophene ring) | (7)-$C_3H_7$(iso) | —H | (S thiophene ring) | (6')-$C_3H_7$(iso) | —H | 778 |
| 191 | (S thiophene ring) | (6)-$C_3H_7$(iso) | —H | (S thiophene ring) | (7')-$C_3H_7$(iso) | —H | 810 |
| 192 | (S thiophene ring) | (7)-$C_3H_7$(iso) | —H | (S thiophene ring) | (6')-$C_3H_7$(iso) | —H | 794 |

TABLE 14-continued

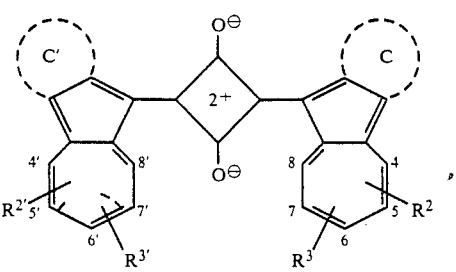

| Example No. | C | (position)-R² | (position)-R³ | C' | (position)-R²' | (position)-R³' | λmax (nm) |
|---|---|---|---|---|---|---|---|
| 193 | (thiophene) | (7)-C₃H₇(iso) | —H | (thiophene) | (7')-C₃H₇(iso) | —H | 799 |
| 194 | (thiophene) | (7)-C₃H₇(iso) | —H | (thiophene) | —H | —H | 779 |
| 195 | (thiophene) | —H | —H | (thiophene) | (7')-C₃H₇(iso) | —H | 795 |
| 196 | (thiophene) | —H | —H | (thiophene) | (7')-C₃H₇(iso) | —H | 761 |
| 197 | (thiophene) | —H | —H | (thiophene) | (7')-C₃H₇(iso) | —H | 795 |
| 198 | (thiophene) | (7)-C₃H₇(iso) | —H | (thiophene) | (7')-C₃H₇(iso) | —H | 765 |
| 199 | (thiophene) | (7)-C₃H₇(iso) | —H | (thiophene) | (7')-C₃H₇(iso) | —H | 799 |
| 200 | (thiophene) | (7)-C₃H₇(iso) | —H | (thiophene) | (7')-C₃H₇(iso) | —H | 781 |

TABLE 14-continued
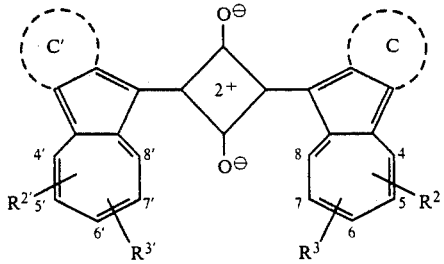
| Example No. | C | (position)-R² | (position)-R³ | C' | (position)-R²' | (position)-R³' | λmax (nm) |
|---|---|---|---|---|---|---|---|
| 201 | 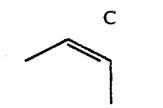 | (7)-C₃H₇(iso) | —H | 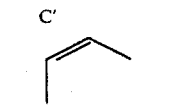 | (7')-C₃H₇(iso) | —H | 815 |
| 202 | 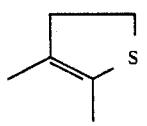 | (7)-C₃H₇(iso) | —H | 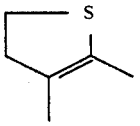 | (7')-C₃H₇(iso) | —H | 781 |
| 203 | 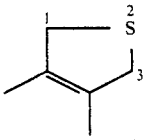 | —H | —H | 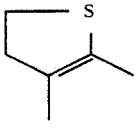 | (6')-C₃H₇(iso) | —H | 790 |
| 204 | 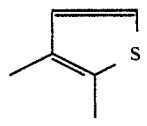 | (7)-C₃H₇(iso) | —H | 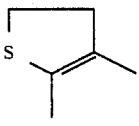 | (6')-C₃H₇(iso) | —H | 794 |
| 205 | 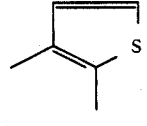 | (7)-C₃H₇(iso) | —H | 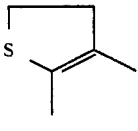 | (6')-C₃H₇(iso) | —H | 775 |
| 206 | 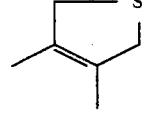 | (7)-C₃H₇(iso) | —H | 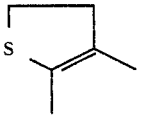 | (6')-C₃H₇(iso) | —H | 810 |
| 207 | 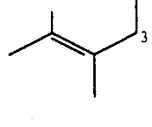 | (6)-C₃H₇(iso) | —H | 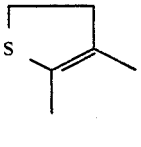 | (6')-C₃H₇(iso) | —H | 788 |
| 208 | 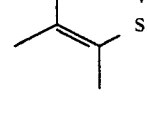 | (6)-C₃H₇(iso) | —H | 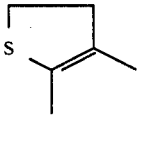 | (7')-C₃H₇(iso) | —H | 759 |

TABLE 14-continued
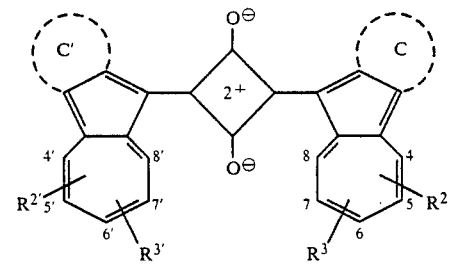
| Example No. | C | (position)-R² | (position)-R³ | C' | (position)-R²' | (position)-R³' | λmax (nm) |
|---|---|---|---|---|---|---|---|
| 209 |  | (6)-C₃H₇(iso) | —H | 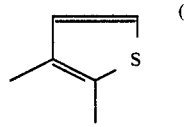 | (7')-C₃H₇(iso) | —H | 794 |
| 210 | 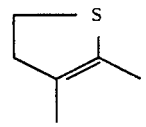 | (6)-C₃H₇(n) | —H | 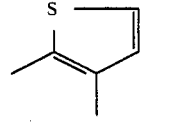 | (6')-C₃H₇(iso) | —H | 772 |
| 211 | 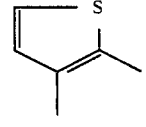 | (6)-C₃H₇(iso) | —H | 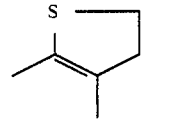 | (6')-C₃H₇(iso) | —H | 804 |
| 212 | 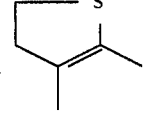 | (4)-OCH₃ | (7)-C₃H₇(iso) | 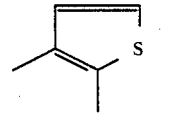 | (4')-OCH₃ | (7')-C₃H₇(iso) | 785 |
| 213 | 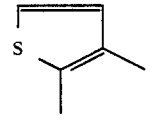 | (5)-C₃H₇(iso) | (8')-CH₃ | 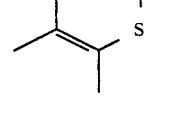 | (5')-C₃H₇(iso) | (8)-CH₃ | 823 |
| 214 | 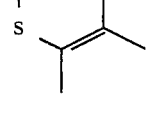 | (7)-C₃H₇(iso) | —H | 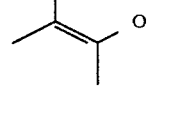 | (6')-C₃H₇(iso) | —H | 756 |
| 215 | 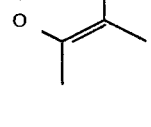 | (5)-C₃H₇(iso) | (8)-CH₃ | 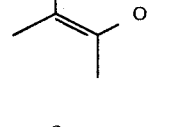 | (5')-C₃H₇(iso) | (8')-CH₃ | 800 |
| 216 | 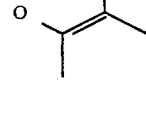 | (4)-CH₃ | (6)-CH₃ | 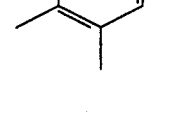 | (7')-C₃H₇(iso) | —H | 795 |

TABLE 14-continued

[Structure: squarylium dye with two azulene/indene systems bearing C and C' substituents, positions 4-8 with R², R³ and 4'-8' with R²', R³', central squarylium (2+ with two O⁻)]

| Example No. | C | (position)-R² | (position)-R³ | C' | (position)-R²' | (position)-R³' | λ_max (nm) |
|---|---|---|---|---|---|---|---|
| 217 | (thiophene ring with methyls) | (4)-CH₃ | (7)-CH₃ | (thiophene ring with methyls) | (4')-CH₃ | (7')-CH₃ | 789 |
| 218 | (thiophene ring with methyls) | (4)-OC₄H₉(n) | (7)-C₃H₇(iso) | (thiophene ring with methyls) | (6')-C₃H₇(iso) | —H | 776 |
| 219 | (thiophene ring with methyls) | —H | —H | (furan ring with methyls) | (7')-C₃H₇(iso) | —H | 768 |
| 220 | (thiophene ring with methyls) | (7)-C₃H₇(iso) | —H | (furan ring with methyls) | (7')-C₃H₇(iso) | —H | 772 |
| 221 | (thiophene ring with methyls) | (7)-C₃H₇(iso) | —H | (furan ring with methyls) | (7')-C₃H₇(iso) | —H | 788 |
| 222 | (thiophene ring with methyls) | (6)-C₃H₇(iso) | —H | (furan ring with methyls) | (7')-C₃H₇(iso) | —H | 753 |
| 223 | (thiophene ring with methyls) | (7)-C₃H₇(iso) | —H | (furan ring with methyls) | (7')-C₃H₇(iso) | —H | 788 |
| 224 | (thiophene ring with methyls) | (6)-C₃H₇(iso) | —H | (furan ring with methyls) | (7')-C₃H₇(iso) | —H | 782 |

TABLE 14-continued
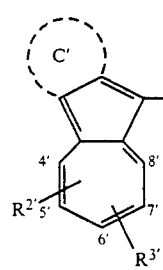
| Example No. | C | (position)-R² | (position)-R³ | C' | (position)-R²' | (position)-R³' | λ_max (nm) |
|---|---|---|---|---|---|---|---|
| 225 | 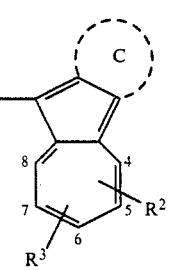 | (7)-C₃H₇(iso) | —H |  | (7')-C₃H₇(iso) | —H | 772 |
| 226 | 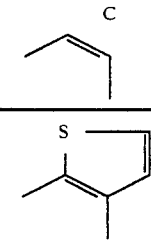 | (7)-C₃H₇(iso) | —H | 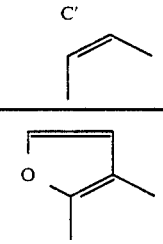 | (7')-C₃H₇(iso) | —H | 768 |
| 227 | 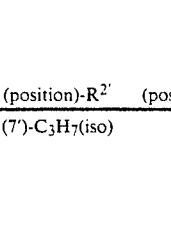 | (7)-C₃H₇(iso) | —H | 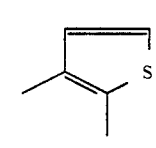 | (7')-C₃H₇(iso) | —H | 787 |
| 228 | 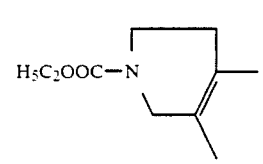 | (6)-C₃H₇(iso) | —H | 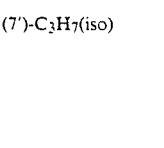 | (7')-C₃H₇(iso) | —H | 766 |
TABLE 15
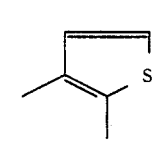
| Ex. No. | C | (position)-R² | (position)-R³ | —R⁵' | —R¹' | (position)-R²' | (position)-R³' | (position)-R⁴' | λ_max (nm) |
|---|---|---|---|---|---|---|---|---|---|
| 229 | 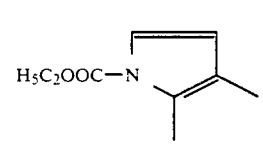 | —H | —H | —H | —H | (8')-CH₃ | (6')-CH₃ | (4')-CH₃ | 768 |

TABLE 15-continued

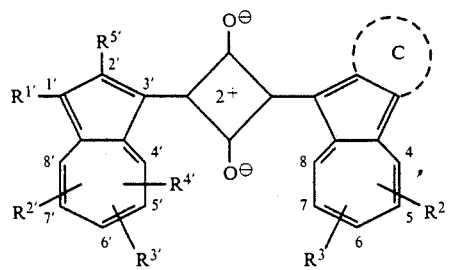

| Ex. No. | C | (position)-R² | (position)-R³ | —R⁵' | —R¹' | (position)-R²' | (position)-R³' | (position)-R⁴' | $\lambda_{max}$ (nm) |
|---|---|---|---|---|---|---|---|---|---|
| 230 | (thiophene with methyls) | (7)-C₃H₇(iso) | —H | —C₂H₅ | —CH₃ | (5')-C₃H₇(iso) | —H | —H | 772 |
| 231 | (thiophene) | (7)-C₃H₇(iso) | —H | —C₃H₇(n) | —C₂H₅ | (5')-C₃H₇(iso) | —H | —H | 788 |
| 232 | (dihydrothiophene) | (7)-C₃H₇(iso) | —H | —C₄H₉(n) | —C₃H₇(n) | (5')-C₃H₇(iso) | —H | —H | 756 |
| 233 | (dihydrothiophene) | (7)-C₃H₇(iso) | —H | —C₆H₁₃(n) | —C₅H₁₁(n) | (6')-C₃H₇(iso) | —H | —H | 791 |
| 234 | (thiophene) | (6)-C₃H₇(iso) | —H | —C₈H₁₇(n) | —C₇H₁₅(n) | (6')-C₃H₇(iso) | —H | —H | 782 |
| 235 | (dihydrofuran) | (7)-C₃H₇(iso) | —H | —C₅H₁₁(n) | —C₄H₉(n) | (5')-C₃H₇(iso) | —H | —H | 760 |
| 236 | (N—COOC₂H₅ ring) | —H | —H | —H | —CH₃ | (5')-C₃H₇(iso) | —H | —H | 761 |
| 237 | (N—COOC₂H₅ ring) | (7)-C₃H₇(iso) | —H | —C₁₃H₂₇(n) | —C₁₂H₂₅(n) | (5')-C₃H₇(iso) | —H | —H | 772 |

TABLE 15-continued

| Ex. No. | C | (position)-R² | (position)-R³ | —R⁵' | —R¹' | (position)-R²' | (position)-R³' | (position)-R⁴' | λ_max (nm) |
|---|---|---|---|---|---|---|---|---|---|
| 238 | (2,3-dimethylthiophene) | —H | —H | —H | —C₃H₇(n) | (5')-C₃H₇(iso) | —H | —H | 752 |
| 239 | (2,3-dimethylthiophene) | (7)-C₃H₇(iso) | —H | —H | —C₈H₁₇(n) | (5')-C₃H₇(iso) | —H | —H | 757 |
| 240 | (2,3-dimethylthiophene) | (7)-C₃H₇(iso) | —H | —H | —C₁₀H₂₁(n) | (5')-C₃H₇(iso) | —H | —H | 772 |
| 241 | (2,3-dimethylthiophene) | (7)-C₃H₇(iso) | —H | —H | —C₁₈H₃₇(n) | (5')-C₃H₇(iso) | —H | —H | 737 |
| 242 | (2,3-dimethylthiophene) | (7)-C₃H₇(iso) | —H | —H | —C₄H₉(n) | (8')-OCH₃ | (5')-C₃H₇(iso) | —H | 774 |
| 243 | (2,3-dimethylthiophene) | (6)-C₃H₇(iso) | —H | —H | —C₃H₇(n) | (8')-OC₇H₁₅(n) | (5')-C₃H₇(iso) | —H | 768 |
| 244 | (2,3-dimethylfuran) | (7)-C₃H₇(iso) | —H | —H | —C₂H₅ | (8')-OC₁₈H₃₇(n) | (5')-C₃H₇(iso) | —H | 746 |
| 245 | (2,3-dimethylthiophene) | (7)-C₃H₇(iso) | —H | —H | —C₅H₁₁(n) | (8')-OC₂H₄OC₂H₅ | (5')-C₃H₇(iso) | —H | 756 |

TABLE 15-continued
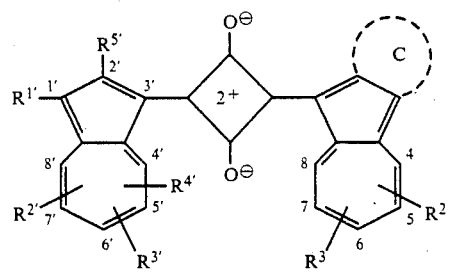
| Ex. No. | C | (position)-R² | (position)-R³ | —R⁵' | —R¹' | (position)-R²' | (position)-R³' | (position)-R⁴' | $\lambda_{max}$ (nm) |
|---|---|---|---|---|---|---|---|---|---|
| 246 | (thiophene) | (7)-C₃H₇(iso) | —H | —H | (phenyl) | (5')-C₃H₇(iso) | —H | —H | 754 |
| 247 | (thiophene) | —H | —H | —H | —CH₂(phenyl) | (5')-C₃H₇(iso) | —H | —H | 750 |
| 248 | (thiophene) | —H | —H | —H | —H | —H | —H | —H | 743 |
| 249 | (thiophene) | (7)-C₃H₇(iso) | —H | —H | —H | (8')-CH₃ | (6')-CH₃ | (4')-CH₃ | 752 |
| 250 | (thiophene) | (7)-C₃H₇(iso) | —H | —H | —CH₃ | (4')-CH₃ | (7')-C₃H₇(iso) | —H | 792 |

TABLE 16

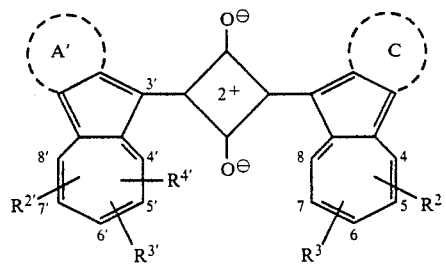

| Example No. | C (structure) | (position)-R² | (position)-R³ | 1',2'-Alkylene Group for Forming Ring A' | (position)-R²' | (position)-R³' | (position)-R⁴' | $\lambda_{max}$ (nm) |
|---|---|---|---|---|---|---|---|---|
| 251 | (thiophene structure) | (7)-C₃H₇(iso) | —H | —(CH₂)₃— | (5')-CH₃ | —H | —H | 749 |
| 252 | (thiophene structure) | (7)-C₃H₇(iso) | —H | —(CH₂)₃— | (6')-C₃H₇(iso) | —H | —H | 783 |
| 253 | (thiophene structure) | (6)-C₃H₇(iso) | —H | —(CH₂)₄— | —H | —H | —H | 781 |
| 254 | (furan structure) | —H | —H | —(CH₂)₄— | (5')-CH₃ | —H | —H | 756 |

TABLE 17

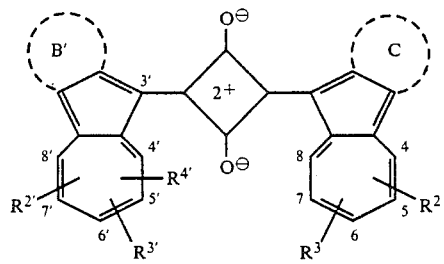

| Example No. | C (structure) | (position)-R² | (position)-R³ | 1',2'-Alkylene Group for Forming Ring B' | (position)-R²' | (position)-R³' | (position)-R⁴' | $\lambda_{max}$ (nm) |
|---|---|---|---|---|---|---|---|---|
| 255 | (furan structure) | (7)-C₃H₇(iso) | —H | —CH=CH—CH=CH— | (5')-C₃H₇(iso) | —H | —H | 793 |

TABLE 17-continued

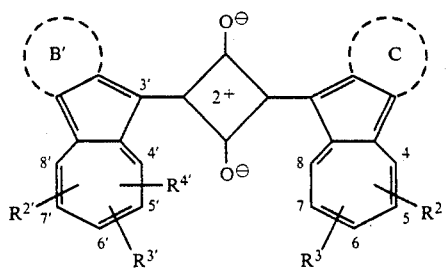

| Example No. | C | (position)-$R^2$ | (position)-$R^3$ | 1',2'-Alkylene Group for Forming Ring B' | (position)-$R^{2'}$ | (position)-$R^{3'}$ | (position)-$R^{4'}$ | $\lambda_{max}$ (nm) |
|---|---|---|---|---|---|---|---|---|
| 256 | (thiophene) | (7)-$C_3H_7$(iso) | —H | —CH=CH—CH=CH— | (8')-$(OC_2H_4)_2OCH_3$ | (5')-$C_3H_7$(iso) | —H | 805 |
| 257 | (thiophene) | (7)-$C_3H_7$(iso) | —H | —CH=CH—CH=CH— | (6')-$C_3H_7$(iso) | —H | —H | 806 |
| 258 | (thiophene) | —H | —H | —CH=CH—C=CH—<br>　　　　　$C_4H_9$(tert) | (5')-$C_3H_7$(iso) | —H | —H | 807 |
| 259 | (thiophene) | (7)-$C_3H_7$(iso) | —H | —CH=CH—C=CH—<br>　　　　　$C_8H_{17}$(n) | (5')-$C_3H_7$(iso) | —H | —H | 812 |
| 260 | (thiophene) | (7)-$C_3H_7$(iso) | —H | —CH=CH—C=CH—<br>　　　　　$OCH_3$ | (5')-$C_3H_7$(iso) | —H | —H | 832 |
| 261 | (thiophene) | (7)-$C_3H_7$(iso) | —H | —CH=C—CH=CH—<br>　　　$OCH_3$ | (5')-$C_3H_7$(iso) | —H | —H | 795 |
| 262 | (thiophene) | (7)-$C_3H_7$(iso) | —H | —CH=CH—C=CH—<br>　　　　　Br | (5')-$C_3H_7$(iso) | —H | —H | 826 |
| 263 | (thiophene) | (6)-$C_3H_7$(iso) | —H | —CH=CH—CH=CH— | (6')-$C_3H_7$(iso) | —H | —H | 815 |

EXAMPLE 264

Thirty milliliters of n-butyl alcohol was added to 15 mg of 3,4-dihydroxy-3-cyclobutene-1,2-dione, and the mixture was heated to about 100° C. to form a solution. To the solution were added 50 mg of 1-n-heptadecylazulene and 15 ml of toluene, and the mixture was stirred at 105° to 110° C. for about 20 minutes while azeotropically removing the produced water. After cooling, the reaction mixture was purified by column chromatography to obtain a compound of the formula:

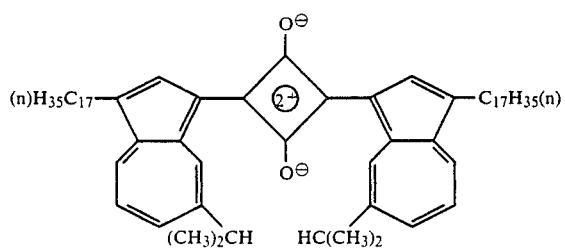

The absorption spectrum of this compound in chloroform is shown in FIG. 1. The maximum absorption wavelength was 726 nm.

EXAMPLES 265 TO 333

In the same manner as described in Example 264, squarilium compounds as shown in Tables 18 to 20 below were prepared. Their structures and the maximum absorption wavelengths in chloroform are shown in Tables 18 to 20.

TABLE 18

| Ex. No. | $-R^5$ | $-R^1$ | (position)-$R^2$ | (position)-$R^3$ | $-R^{5'}$ | $-R^{1'}$ | (position)-$R^{2'}$ | (position)-$R^{3'}$ | $\lambda_{max}$ (nm) |
|---|---|---|---|---|---|---|---|---|---|
| 265 | —H | —$C_{14}H_{29}$(n) | —H | —H | —H | —$C_{14}H_{29}$(n) | —H | —H | 712 |
| 266 | —H | —$C_{18}H_{37}$(n) | —H | —H | —H | —$C_{18}H_{37}$(n) | —H | —H | 712 |
| 267 | —H | —$C_{20}H_{41}$(n) | —H | —H | —H | —$C_{20}H_{41}$(n) | —H | —H | 712 |
| 268 | —H | —$C_{23}H_{47}$(n) | —H | —H | —H | —$C_{23}H_{47}$(n) | —H | —H | 712 |
| 269 | —H | —$C_{17}H_{35}$(n) | (5)-$CH_3$ | —H | —H | —$C_{17}H_{35}$(n) | (5')-$CH_3$ | —H | 726 |
| 270 | —H | —$C_{20}H_{41}$(n) | (5)-$CH_3$ | —H | —H | —$C_{20}H_{41}$(n) | (5')-$CH_3$ | —H | 726 |
| 271 | —H | —$C_{14}H_{29}$(n) | (5)-$C_3H_7$(iso) | —H | —H | —$C_{14}H_{29}$(n) | (5')-$C_3H_7$(iso) | —H | 726 |
| 272 | —H | —$C_{19}H_{39}$(n) | (5)-$C_3H_7$(iso) | —H | —H | —$C_{19}H_{39}$(n) | (5')-$C_3H_7$(iso) | —H | 726 |
| 273 | —H | —$C_{24}H_{49}$(n) | (5)-$C_3H_7$(iso) | —H | —H | —$C_{24}H_{49}$(n) | (5')-$C_3H_7$(iso) | —H | 726 |
| 274 | —H | —$C_{18}H_{37}$(n) | (6)-$CH_3$ | —H | —H | —$C_{18}H_{37}$(n) | (6')-$CH_3$ | —H | 732 |
| 275 | —H | —$C_{21}H_{43}$(n) | (6)-$CH_3$ | —H | —H | —$C_{21}H_{43}$(n) | (6')-$CH_3$ | —H | 732 |
| 276 | —H | —$C_{15}H_{31}$(n) | (6)-$C_3H_7$(iso) | —H | —H | —$C_{15}H_{31}$(n) | (6')-$C_3H_7$(iso) | —H | 732 |
| 277 | —H | —$C_{17}H_{35}$(n) | (6)-$C_3H_7$(iso) | —H | —H | —$C_{17}H_{35}$(n) | (6')-$C_3H_7$(iso) | —H | 732 |
| 278 | —$C_{15}H_{31}$(n) | —$C_{14}H_{29}$(n) | (5)-$C_3H_7$(iso) | —H | —$C_{15}H_{31}$(n) | —$C_{14}H_{29}$(n) | (5')-$C_3H_7$(iso) | —H | 758 |
| 279 | —$C_{17}H_{35}$(n) | —$C_{16}H_{33}$(n) | (5)-$C_3H_7$(iso) | —H | —$C_{17}H_{35}$(n) | —$C_{16}H_{33}$(n) | (5')-$C_3H_7$(iso) | —H | 758 |
| 280 | —H | —$C_{23}H_{47}$(n) | —H | —H | —$C_2H_5$ | —$CH_3$ | (5')-$C_3H_7$(iso) | —H | 735 |
| 281 | —H | —$C_{19}H_{39}$(n) | —H | —H | —$C_3H_7$(n) | —$C_2H_5$ | (5')-$C_3H_7$(iso) | —H | 735 |
| 282 | —H | —$C_{15}H_{31}$(n) | (5)-$CH_3$ | —H | —$C_3H_7$(n) | —$C_2H_5$ | (5')-$C_3H_7$(iso) | —H | 742 |
| 283 | —H | —$C_{16}H_{33}$(n) | (5)-$C_3H_7$(iso) | —H | —$C_4H_9$(n) | —$C_3H_7$(n) | (5')-$C_3H_7$(iso) | —H | 742 |
| 284 | —H | —$C_{19}H_{39}$(n) | (5)-$C_3H_7$(iso) | —H | —$C_8H_{17}$(n) | —$C_7H_{15}$(n) | (5')-$CH_3$ | —H | 742 |
| 285 | —H | —$C_{21}H_{43}$(n) | (5)-$C_3H_7$(iso) | —H | —$C_2H_5$ | —$CH_3$ | (5')-$CH_3$ | —H | 742 |
| 286 | —H | —$C_{17}H_{35}$(n) | (6)-$CH_3$ | —H | —$C_4H_9$(n) | —$C_3H_7$(n) | (5')-$C_3H_7$(iso) | —H | 745 |
| 287 | —H | —$C_{20}H_{41}$(n) | (6)-$C_3H_7$(iso) | —H | —$C_5H_{11}$(n) | —$C_4H_9$(n) | (5')-$CH_3$ | —H | 745 |
| 288 | —H | —$C_{18}H_{37}$(n) | (6)-$C_3H_7$(iso) | —H | —$C_6H_{13}$(n) | —$C_5H_{11}$(n) | (5')-$C_3H_7$(iso) | —H | 745 |

TABLE 18-continued

| Ex. No. | —R⁵ | —R¹ | (position)-R² | (position)-R³ | —R⁵' | —R¹' | (position)-R²' | (position)-R³' | λmax (nm) |
|---|---|---|---|---|---|---|---|---|---|
| 289 | —H | —C₁₆H₃₃(n) | —H | —H | —H | –C₆H₅ | (5')-C₃H₇(iso) | —H | 730 |
| 290 | —H | —C₂₀H₄₁(n) | —H | —H | —H | —CH₂C₆H₅ | (5')-C₃H₇(iso) | —H | 719 |
| 291 | —H | —C₂₄H₄₉(n) | (5)-CH₃ | —H | —H | –C₆H₅ | (5')-C₃H₇(iso) | —H | 737 |
| 292 | —H | —C₁₉H₃₉(n) | (5)-C₃H₇(iso) | —H | —H | –C₆H₅ | (5')-CH₃ | —H | 736 |
| 293 | —H | —C₁₅H₃₁(n) | (5)-C₃H₇(iso) | —H | —H | —CH₂C₆H₅ | (6')-C₃H₇(iso) | —H | 728 |
| 294 | —H | —C₂₃H₄₇(n) | (5)-C₃H₇(iso) | —H | —H | —CH₂-C₆H₄-CH₃ | (5')-C₃H₇(iso) | —H | 726 |
| 295 | —H | —C₁₇H₃₅(n) | (6)-CH₃ | —H | —H | –C₆H₅ | (5')-C₃H₇(iso) | —H | 740 |
| 296 | —H | —C₁₄H₂₉(n) | (6)-C₃H₇(iso) | —H | —H | –C₆H₄-C₄H₉(n) | (5')-C₃H₇(iso) | —H | 740 |
| 297 | —H | —C₂₂H₄₅(n) | (6)-C₃H₇(iso) | —H | —H | —CH₂C₆H₅ | (6')-C₃H₇(iso) | —H | 729 |
| 298 | —H | —C₁₇H₃₅(n) | —H | —H | —H | —C₅H₁₁(n) | (5')-C₃H₇(iso) | (8')-OCH₃ | 721 |
| 299 | —H | —C₂₄H₄₉(n) | —H | —H | —H | —C₄H₉(n) | (5')-C₃H₇(iso) | (8')-OC₇H₁₅(n) | 721 |
| 300 | —H | —C₂₀H₄₁(n) | (5)-CH₃ | —H | —H | —C₆H₁₃(n) | (5')-C₃H₇(iso) | (8')-OCH₃ | 728 |
| 301 | —H | —C₁₅H₃₁(n) | (5)-C₃H₇(iso) | —H | —H | —C₄H₉(n) | (5')-C₃H₇ | (8')-OCH₃ | 728 |
| 302 | —H | —C₁₄H₂₉(n) | (5)-C₃H₇(iso) | —H | —H | —CH₃ | (4')-CH₃ | (7')-C₃H₇(iso) | 747 |
| 303 | —H | —C₂₁H₄₃(n) | (5)-C₃H₇(iso) | —H | —H | —C₅H₁₁(n) | (5')-C₃H₇(iso) | (8')-OC₂H₄OC₂H₅ | 728 |

TABLE 18-continued

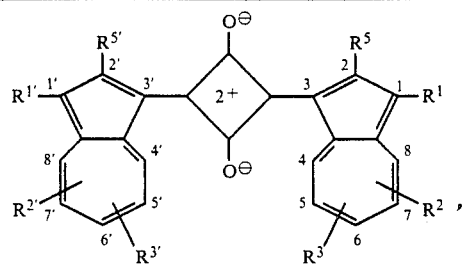

| Ex. No. | −R⁵ | −R¹ | (position)-R² | (position)-R³ | −R⁵' | −R¹' | (position)-R²' | (position)-R³' | λmax (nm) |
|---|---|---|---|---|---|---|---|---|---|
| 304 | −H | −C₁₆H₃₃(n) | (6)-CH₃ | −H | −H | −C₃H₇(n) | (5')-C₃H₇(iso) | (8')-OCH₃ | 731 |
| 305 | −H | −C₂₃H₄₇(n) | (6)-C₃H₇(iso) | −H | −H | −C₅H₁₁(n) | (5')-C₃H₇(iso) | (8')-OCH₃ | 731 |
| 306 | −H | −C₁₉H₃₉(n) | (6)-C₃H₇(iso) | −H | −H | −C₄H₉(n) | (5')-C₃H₇(iso) | (8')-OC₇H₁₅(n) | 731 |
| 307 | −H | −C₂₀H₄₁(n) | −H | −H | −H | −C₁₄H₂₉(n) | (5')-C₃H₇(iso) | −H | 719 |
| 308 | −H | −C₂₃H₄₇(n) | −H | −H | −H | −C₁₉H₃₉(n) | (5')-C₃H₇(iso) | −H | 719 |
| 309 | −H | −C₁₄H₂₉(n) | (5)-CH₃ | −H | −H | −C₁₇H₃₅(n) | (6')-CH₃ | −H | 729 |
| 310 | −H | −C₁₉H₃₉(n) | (5)-C₃H₇(iso) | −H | −H | −C₂₀H₄₁(n) | (5')-CH₃ | −H | 726 |
| 311 | −H | −C₂₁H₄₃(n) | (5)-C₃H₇(iso) | −H | −H | −C₁₅H₃₁(n) | −H | −H | 719 |
| 312 | −H | −C₂₅H₅₁(n) | (5)-C₃H₇(iso) | −H | −H | −C₁₄H₂₉(n) | −H | −H | 719 |
| 313 | −H | −C₁₆H₃₃(n) | (6)-CH₃ | −H | −H | −C₂₄H₄₉(n) | (5')-C₃H₇(iso) | −H | 729 |
| 314 | −H | −C₁₅H₃₁(n) | (6)-C₃H₇(iso) | −H | −H | −C₁₉H₃₉(n) | (5')-C₃H₇(iso) | −H | 729 |
| 315 | −H | −C₁₈H₃₇(n) | (6)-C₃H₇(iso) | −H | −H | −C₁₄H₂₉(n) | (5')-CH₃ | −H | 729 |

TABLE 19

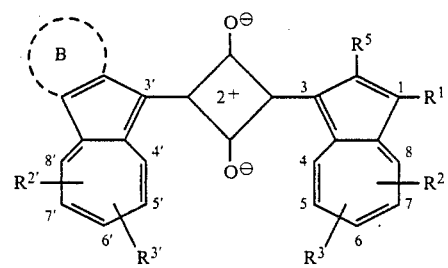

| Example No. | −R⁵ | −R¹ | (position)-R² | (position)-R³ | 1',2'-Alkylene Group for Forming Ring B | (position)-R²' | (position)-R³' | λmax (nm) |
|---|---|---|---|---|---|---|---|---|
| 316 | −H | −C₁₅H₃₁(n) | −H | −H | −CH=CH−C=CH−<br>\|<br>C₃H₇(n) | (5')-C₃H₇(iso) | −H | 774 |
| 317 | −H | −C₂₅H₅₁(n) | −H | −H | −CH=CH−C=CH−<br>\|<br>C₄H₉(n) | (5')-C₃H₇(iso) | −H | 774 |
| 318 | −H | −C₁₇H₃₅(n) | (5)-CH₃ | −H | −CH=CH−CH=CH− | (5')-C₃H₇(iso) | −H | 775 |
| 319 | −H | −C₂₃H₄₇(n) | (5)-C₃H₇(iso) | −H | −CH=CH−C=CH−<br>\|<br>C₂H₅ | (6')-C₃H₇(iso) | −H | 784 |
| 320 | −H | −C₁₉H₃₉(n) | (5)-C₃H₇(iso) | −H | −CH=CH−C=CH−<br>\|<br>C₄H₉(n) | (5')-C₃H₇(iso) | −H | 781 |
| 321 | −H | −C₂₁H₄₃(n) | (5)-C₃H₇(iso) | −H | −CH=C−CH=CH−<br>\|<br>OCH₃ | (5')-C₃H₇(iso) | −H | 783 |

TABLE 19-continued

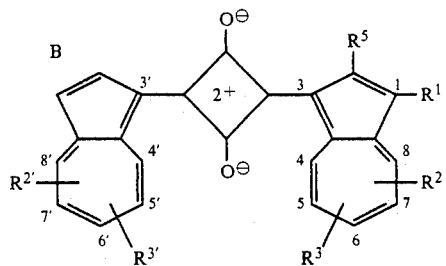

| Example No. | —R⁵ | —R¹ | (position)-R² | (position)-R³ | 1',2'-Alkylene Group for Forming Ring B | (position)-R²' | (position)-R³' | $\lambda_{max}$ (nm) |
|---|---|---|---|---|---|---|---|---|
| 322 | —H | —C$_{18}$H$_{37}$(n) | (6)-CH$_3$ | —H | —CH=CH—C(C$_2$H$_5$)=CH— | (5')-C$_3$H$_7$(iso) | —H | 778 |
| 323 | —H | —C$_{20}$H$_{41}$(n) | (6)-C$_3$H$_7$(iso) | —H | —CH=CH—C(C$_7$H$_{15}$(n))=CH— | (5')-C$_3$H$_7$(iso) | —H | 784 |
| 324 | —H | —C$_{16}$H$_{33}$(n) | (6)-C$_3$H$_7$(iso) | —H | —CH=CH—C(C$_4$H$_9$(n))=CH— | (6')-C$_3$H$_7$(iso) | —H | 787 |

TABLE 20

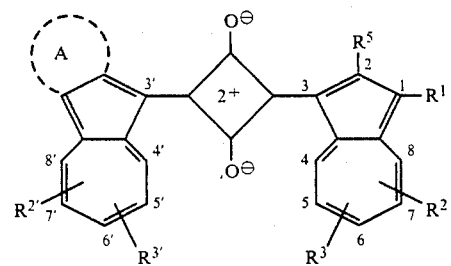

| Example No. | —R⁵ | —R¹ | (position)-R² | (position)-R³ | 1',2'-Alkylene Group for Forming Ring A | (position)-R²' | (position)-R³' | $\lambda_{max}$ (nm) |
|---|---|---|---|---|---|---|---|---|
| 325 | —H | —C$_{24}$H$_{49}$(n) | —H | —H | ŧCH$_2$ŧ$_3$ | (5')-C$_3$H$_7$(iso) | —H | 727 |
| 326 | —H | —C$_{22}$H$_{45}$(n) | —H | —H | ŧCH$_2$ŧ$_4$ | (5')-CH$_3$ | —H | 735 |
| 327 | —H | —C$_{14}$H$_{29}$(n) | (5)-CH$_3$ | —H | ŧCH$_2$ŧ$_3$ | (5')-C$_3$H$_7$(iso) | —H | 742 |
| 328 | —H | —C$_{17}$H$_{35}$(n) | (5)-C$_3$H$_7$(iso) | —H | ŧCH$_2$ŧ$_3$ | (5')-C$_3$H$_7$(iso) | —H | 742 |
| 329 | —H | —C$_{20}$H$_{41}$(n) | (5)-C$_3$H$_7$(iso) | —H | ŧCH$_2$ŧ$_3$ | (5')-CH$_3$ | —H | 734 |
| 330 | —H | —C$_{23}$H$_{47}$(n) | (5)-C$_3$H$_7$(iso) | —H | ŧCH$_2$ŧ$_3$ | (6')-C$_3$H$_7$(iso) | —H | 744 |
| 331 | —H | —C$_{15}$H$_{31}$(n) | (6)-CH$_3$ | —H | ŧCH$_2$ŧ$_4$ | (5')-C$_3$H$_7$(iso) | —H | 745 |
| 332 | —H | —C$_{18}$H$_{37}$(n) | (6)-C$_3$H$_7$(iso) | —H | ŧCH$_2$ŧ$_4$ | (5')-C$_3$H$_7$(iso) | —H | 745 |
| 333 | —H | —C$_{21}$H$_{43}$(n) | (6)-C$_3$H$_7$(iso) | —H | ŧCH$_2$ŧ$_4$ | (6')-C$_3$H$_7$(iso) | —H | 747 |

While the invention has been described in detail and with reference to specific embodiments thereof, it will be apparent to one skilled in the art that various changes and modifications can be made therein without departing from the spirit and scope thereof.

What is claimed is:

1. A squarilium compound represented by the formula (I):

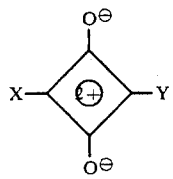

wherein X represents

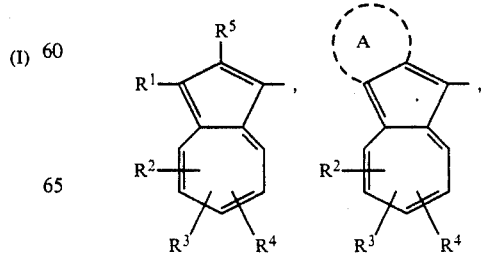

-continued

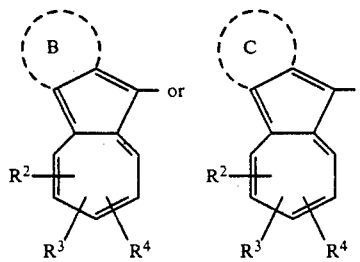

and Y represents

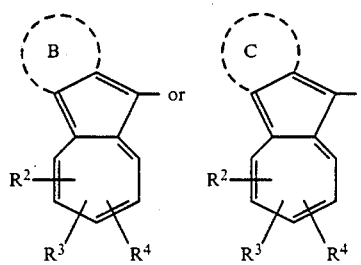

wherein $R^1$ represents a hydrogen atom, a $C_{1-25}$ alkyl group, a phenyl group which is or is not substituted by a $C_{1-25}$ alkyl group, a $C_{1-13}$ alkoxy group, or halogen atom, a naphthyl group, a benzyl group which is or is not substituted by an alkyl group, an alkoxy group or a halogen atom, or a phenethyl group; $R^2$, $R^3$ and $R^4$ each represents a hydrogen atom, a $C_{1-5}$ alkyl group or an alkoxy group having total carbon number of 1 to 20 which is or is not substituted by an alkoxy group; $R^5$ represents a hydrogen atom or a $C_{1-13}$ alkyl group; ring A represents a cyclic alkylene of 5 or 6 members which is not substituted by an alkyl group; ring B represents an aromatic ring or an 1,2-alkenylene ring which are or are not substituted by a halogen atom and are not substituted by an alkyl group or alkoxy group; and ring C represents a heterocyclic ring containing one of a nitrogen atom, an oxygen atom and a sulfur atom and said heterocyclic ring is not substituted by an alkyl group; with the proviso that X and Y are not the same when either one of them represents

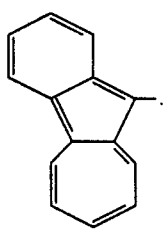

2. A squarilium compound represented by the formula (I):

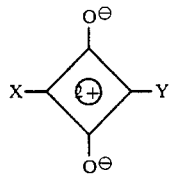 (I)

wherein X represents

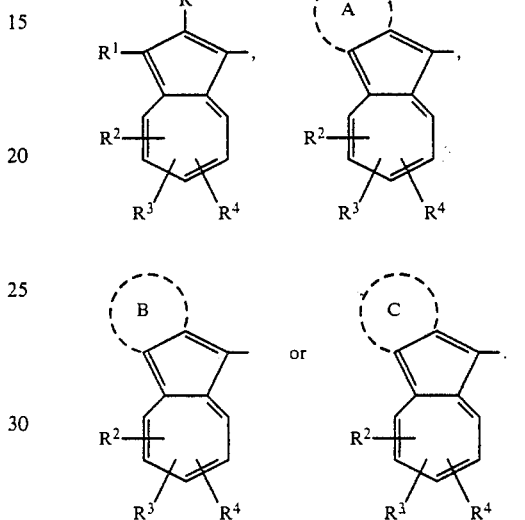

wherein $R^1$ represents a hydrogen atom, a $C_{1-25}$ alkyl group, a phenyl group or a benzyl group; $R^2$, $r^3$ and $R^4$ each represents a hydrogen atom, an alkyl group or an alkoxy group having 1 to 13 carbon atoms which is or is not substituted by an alkoxy group; $r^5$ represents a hydrogen atom or a $C_{1-20}$ alkyl group; ring A represents a cyclic alkylene of 5 or 6 members and is not substituted by an alkyl group; ring B represents an 1,2-alkenylene ring of 6 members which is not substituted by an alkyl group or an alkoxy group; and ring C represents a heterocyclic ring of 5 or 6 members containing one of a nitrogen atom, an oxygen atom and a sulfur atom and said heterocyclic ring is not substituted by alkyl group; and Y represents

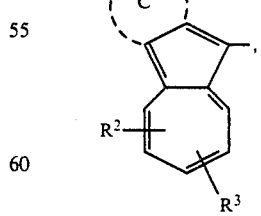

wherein $R^2$, $R^3$ and ring C are as defined above in this claim.

3. A squarilium compound as in claim 2, wherein at least one of X and Y represents a group selected from the group (I) and (II), Group (I):

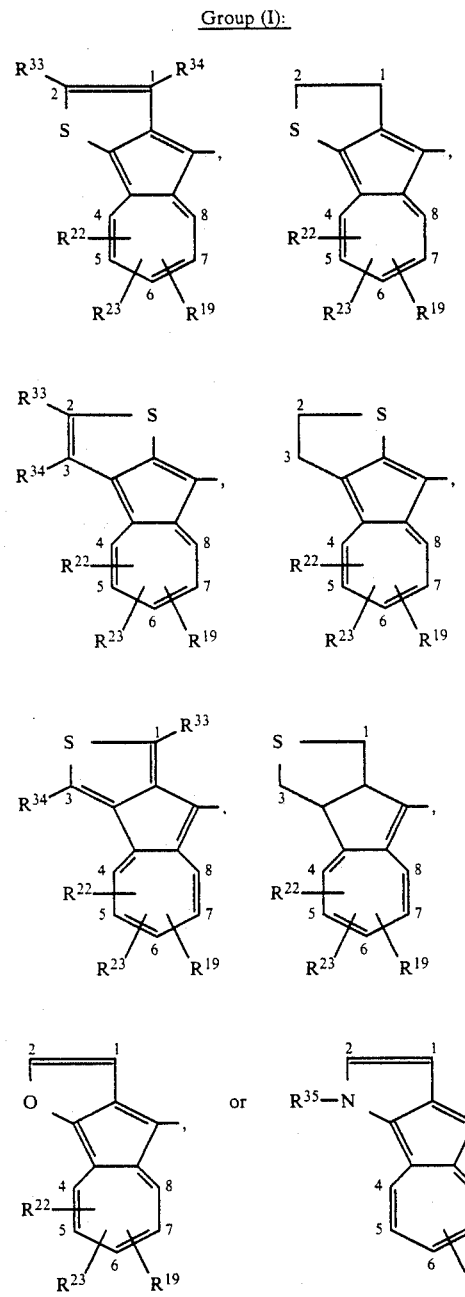

Group (II):

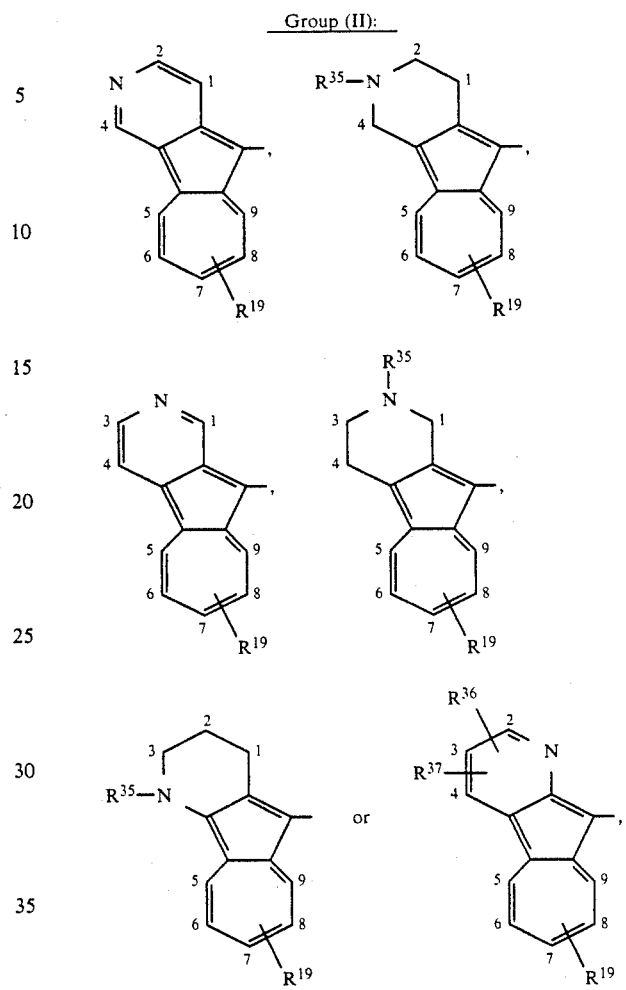

wherein $R^{19}$ is as defined above in this claim; $R^{35}$ is as defined above; $R^{36}$ and $R^{37}$ each represents a hydrogen atom, a halogen atom, an alkoxy group, an alkylamino group, an alkoxycarbonyl group or a cyano group; with the proviso that $R^{19}$ is at the 7- or 8-position.

4. A squarilium compound represented by the formula

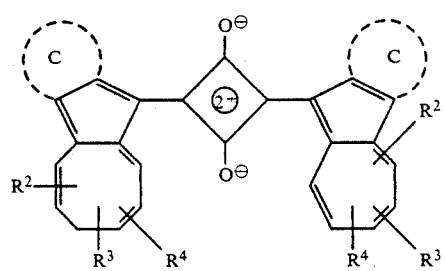

wherein $R^{19}$ represents a hydrogen atom, a methyl group or an isopropyl group; $R^{22}$ and $R^{23}$ each represents a hydrogen atom, an alkyl group having from 1 to 13 carbon atoms or an alkoxy-substituted or unsubstituted alkoxy group having from 1 to 13 carbon atoms; $R^{33}$ and $R^{34}$ each represents a hydrogen atom, a methyl group, or a phenyl group; and $R^{35}$ represents a hydrogen atom or an alkoxycarbonyl group; with the proviso that $R^{19}$ is at the 6- or 7-position, and at least one of $R^{19}$, $R^{22}$ and $R^{23}$ represents a hydrogen atom, wherein ring C represents a heterocyclic ring containing one of a nitrogen atom, an oxygen atom or a sulfur atom and said heterocyclic ring is not substituted by an alkyl group and $R^2$, $R^3$ and $R^4$ each represents a hydrogen atom, an alkyl group or an alkoxy-substituted or unsubstituted alkoxy group.

5. A squarilium compound as in claim 4, wherein ring C represents a five or six-membered heterocyclic ring containing a sulfur atom, $R^2$ represents a hydrogen atom and R³ and R⁴ each represents a hydrogen atom, an alkyl group or an alkoxy group.

6. A squarilium compound as in claim 5, wherein the compound is represented by the formula:

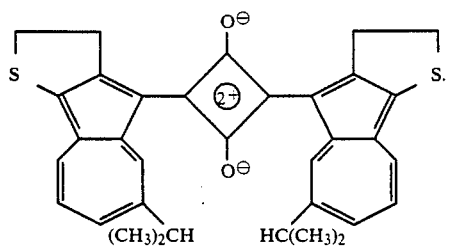

7. A squarilium compound as in claim 5, wherein the compound is represented by the formula:

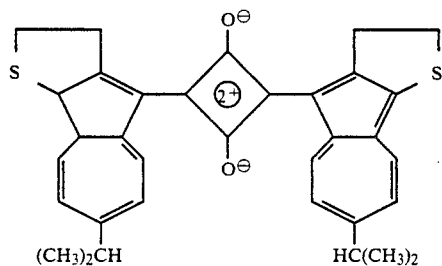

8. A liquid crystal composition comprising a host liquid crystalline material and further comprising a squarilium compound as in claim 1.

9. A liquid crystal composition comprising a host liquid crystalline material and further comprising a squarilium compound as in claim 2.

10. A squarilium compound as in claim 2, wherein Y represents

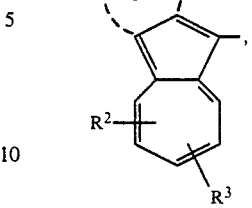

wherein ring C represents a heterocyclic ring containing a sulfur atom and R² and R³ are defined in claim 2.

11. A squarilium compound as in claim 2, wherein X and Y each represents

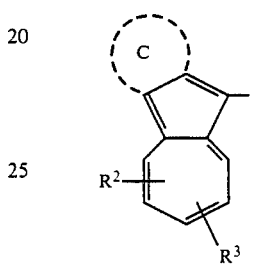

wherein ring C represents a heterocyclic ring containing a sulfur atom and R² and R³ each represents a hydrogen atom, an alkyl group or an alkoxy group.

12. A squarilium compound as in claim 5, wherein ring C represents a thiophene or dihydrothiophene ring.

13. A squarilium compound as in claim 5, wherein ring C represents a dihydrothiophene ring; R² is a hydrogen atom and R³ is an alkyl group.

* * * * *